(12) United States Patent
Hotta et al.

(10) Patent No.: US 6,355,365 B1
(45) Date of Patent: Mar. 12, 2002

(54) MOLECULAR COMPOUND, LUMINOUS MATERIAL USING THE SAME, AND LUMINOUS ELEMENT

(75) Inventors: Shu Hotta, Kawasaki; Takashi Tamaki, Ibaragi-ken, both of (JP)

(73) Assignees: Japan Chemical Innovation Institute; Agency of Industrial Science & Technology, both of Tokyo (JP)

( * ) Notice: Subject to any disclaimer, the term of this patent is extended or adjusted under 35 U.S.C. 154(b) by 0 days.

(21) Appl. No.: 09/307,905

(22) Filed: May 10, 1999

(30) Foreign Application Priority Data

May 8, 1998 (JP) .......................................... 10-126465

(51) Int. Cl.$^7$ ...................... H05B 33/14; C07D 333/00
(52) U.S. Cl. .................. 428/690; 428/917; 428/704; 313/504; 313/506; 549/1; 549/29; 549/41; 549/80; 526/256
(58) Field of Search ................................ 549/1, 29, 41, 549/80; 526/256; 428/917, 690, 704; 313/504, 506

(56) References Cited

U.S. PATENT DOCUMENTS 5,142,343 A * 8/1992 Hosokawa et al. ........... 357/17

OTHER PUBLICATIONS

Graf et al. Synthesis and Characterization of Cyclopentadienyl and Pentamethylcyclopentadienyl Ruthenium Complexes of Oligothiophenes (Inorganic Chemistry 1995, 34, 1562–1575).*

* cited by examiner

Primary Examiner—Cynthia H. Kelly
Assistant Examiner—Ling Xu
(74) Attorney, Agent, or Firm—Browdy and Neimark

(57) ABSTRACT

Provided is a new molecular compound excellent in luminous property, which has a molecular structure wherein a thiophene ring and a benzene (or naphthalene) ring are directly bonded to each other, as a molecular compound making it possible to control its luminous color relatively easily and realize highly efficient and bright luminescence. In this compound, its color tone of emitted light can be variously changed by altering the number of the thiophene ring and the benzene (or naphthalene) ring and the bonding order of the rings. Thus, if this molecular compound is used as a luminous material, it is possible to easily cope with both control of its luminous color and realization of highly efficient and bright luminescence. Use of a luminous material using this molecular compound makes it possible to realize luminescence having wide colors from violet to red highly efficiently.

3 Claims, 17 Drawing Sheets

MOLECULAR COMPOUND, LUMINOUS MATERIAL USING THE SAME, AND LUMINOUS ELEMENT

BACKGROUND OF THE INVENTION

1. Field of the Invention

The present invention relates to a new functional molecular compound which can be used in the chemical industry and the electrical industry, and an application technique thereof as a luminous material and a luminous element.

2. Description of the Prior Art

An organic electro luminescence (EL) device using a functional organic material was suggested in the past. Since then, various materials have been developed for the purpose of improving the luminous efficiency of the organic electro luminescence device, controlling its luminous color, and the like. These techniques are described in, for example, J. Appl. Phys. 65, 3610 (1989), W. Tang, S. A. Van Slyke, and C. H. Chen.

However, the performance of organic EL devices using materials which have been developed up to the present is insufficient for practical use. The main reason for it is that it is difficult to cope with both of control of the luminous color by a molecular compound (any one of low molecular compounds, oligomers and polymers) constituting a functional organic compound and effective luminescence having a high brightness by using the molecular compound. In other words, concerning conventional materials, for example, aluminoquinoline low molecular compounds, which are widely used, luminescence having high brightness and efficiency is relatively easy, but the control of their luminous color is difficult. Concerning compounds wherein the conjugation length of their electric system is changed to control their luminous color, such as oligothiophen, it is difficult to realize luminescence having high efficiency and brightness.

In order to overcome these problems, new compounds wherein an oligothiophen segment is combined with a triphenylamine segment are also suggested (Lecture Proceeding I, p129, 1998, The Japan Chemical Society, 74th, Annual Convention in spring, Tetsuya Noda, Hiromitsu Ogawa, Naoki Noma, and Yasuhiko Shirota). However, these compounds do not satisfactorily overcome the problems.

These situations are described in, for example, Handbook of Organic Conductive Molecules and Polymers, S. Hotta, (Ed. H. S. Nalwa), Chichester, 1997, Vol. 2, Chapter 8, John Wiley & Sons, and Lecture Proceeding I, p129, 1998, The Japan Chemical Society, 74th, Annual Convention in spring, Katsuyuki Ogura, Motohiro Akazome, Tetsu Tanaka and Tatsuo Fukuda.

SUMMARY OF THE INVENTION

An object of the present invention is to provide molecular compounds making it possible to control their luminous color relatively easily and realize highly efficient and bright luminescence; and luminous materials using a series of molecular compounds.

The present invention provides a series of molecular compounds making it possible to overcome the above-mentioned problems, and cope with both of control of their luminous color and realization of highly efficient and bright luminescence; and luminous materials using a series of molecular compound. These molecular compounds include entirely new compounds and compounds which have already been known but whose effect of coping with both of the control of their luminous color and highly efficient and bright luminescence has not been recognized up to the present.

The feature of all molecular compounds according to the present invention is in that their thiophene ring and benzene ring are directly bonded to each other. Their luminous color can easily be controlled by changing the number of these rings and the bonding order of these rings. Consequently, these molecular compounds are used to make it possible to realize luminescence having wide colors from violet to red highly efficiently and brightly. This effect is based on the fact that the conjugation length of the electric system in these compounds can be changed at will.

The feature of another kind of molecular compounds according to the present invention is in that their thiophene ring and naphthalene ring are directly bonded to each other. Their luminous color can easily be controlled by changing the number of these rings and the bonding order of these rings. Consequently, these molecular compounds are used to make it possible to realize luminescence having wide luminous colors highly efficiently and brightly in the same way as the molecular compounds comprising a thiophene ring and a benzene ring. This effect is also based on the fact that the conjugation length or the electronic system in these compounds can be changed at will.

A first aspect of the present invention is a molecular compound having the following molecular structure:

[Compound 15]

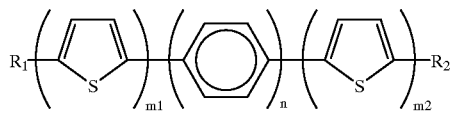

wherein R1 and R2 each independently represents any one of hydrogen, an alkyl group, an alkenyl group and a halogen; and m1, m2 and n are 1 or more provided that when n is 1 or 2, at least one of m1 and m2 is 2 or more, and when n is 3 or more, m1 and m2 are 1 or more. The molecular compound has the effect of realizing a luminous material which emits light having a very high brightness and in which its color changes variously in accordance with the number of m1, m2 and n.

A second aspect of the present invention is a molecular compound having the following molecular structure:

[Compound 16]

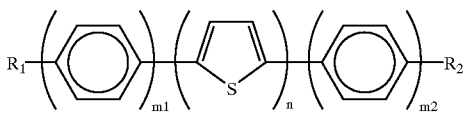

wherein R1 and R2 each independently represents any one of hydrogen, an alkyl group, an alkenyl group and a halogen; and m1, m2 and n are 1 or more provided that when n is 1 or 2, at least one of m1 and m2 is 2 or more, and when n is 3 or more, m1 and m2 are 1 or more. The molecular compound has the effect of realizing a luminous material which emits light having a very high brightness and in which its color changes variously in accordance with the number of m1, m2 and n.

A third aspect of the present invention is a molecular compound having the following molecular structure:

[Compound 17]

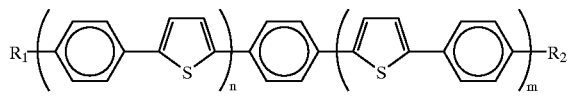

wherein R1 and R2 each independently represents any one of hydrogen, an alkyl group, an alkenyl group and a halogen; and n and m are 1 or more. The molecular compound has the effect of realizing a luminous material which emits light having a far higher brightness by alternate arrangemnent of the thiophen rings and the benzene rings, and in which its color changes variously in accordance with the number of in and n.

A forth aspect of the present invention is a molecular compound having the following molecular structure:

[Compound 18]

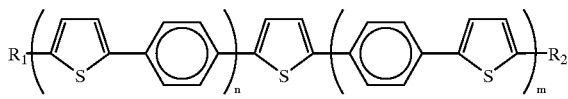

wherein R1 and R2 each independently represents any one of hydrogen, an alkyl group, an alkenyl group and a halogen; and/or more. The molecular compound has the effect of realizing a luminous material which emits light having a far higher brightness by alternate arrangement of the thiophene rings and the benzene rings, and in which its color changes variously in accordance with the number of m and n.

A fifth aspect of the present invention is a molecular compound having the following molecular structure:

[Compound 19]

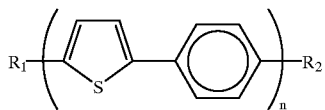

wherein R1 and R2 each independently represents any one of hydrogen, an alkyl group, an alkenyl group and a halogen; and n is 2 or more. The molecular compound has the effect of realizing a luminous material which emits light having a far higher brightness by alternate arrangement of the thiophene rings and the benzene rings, and in which its color changes variously in accordance with the number of n.

A sixth aspect of the present invention is a molecular compound having the following molecular structure:

[Compound 20]

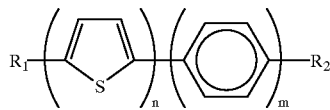

wherein R1 and R2 each independently represents any one of hydrogen, an alkyl group, an alkenyl group and a halogen; and at least one of n and m is 2 or more. The molecular compound has the effect of realizing a luminous material which emits light having a very high brightness, and in which its color changes variously in accordance with the number of m and n.

A seventh aspect of the present invention is a luminous material comprising a molecular compound having a molecular structure wherein a thiophene ring and a benzene ring are directly bonded to each other. This material has the effect of giving luminous color having a high brightness.

An eighth aspect of the present invention is a luminous material according to the seventh aspect, wherein the number of the thiopheraring and the benzene ring and the bonding order of the rings are changed. This material has the effect that its luminous color is controlled and light of various color tones are emitted with a high brightness.

A ninth aspect of the present invention is a luminous material according to the seventh or eight aspect, wherein the bonding order of the thiophene ring and the benzene ring is determined to arrange both the rings alternately. The material has the effect of giving a far higher brightness than luminous materials using a molecular compound wherein other bonding orders of the thiophene ring and the benzene ring are adopted.

A tenth aspect of the present invention is a luminous material using a molecular compound having the following molecular structure:

[Compound 21]

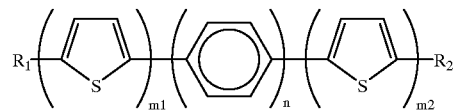

wherein R1 and R2 each independently represents any one of hydrogen, an alkyl group, an alkenyl group and a halogen; and n, m1 and m2 are 1 or more. The material has the effect of realizing a luminous material which emits light having a very high brightness and in which its color changes variously in accordance with the number of m1, m2 and n.

An eleventh aspect of the present invention is a luminous material using a molecular compound having the following molecular structure:

[Compound 22]

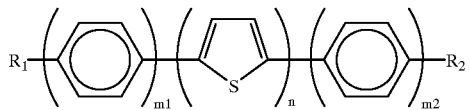

wherein R1 and R2 each independently represents any one of hydrogen, an alkyl group, an alkenyl group and a halogen; and n, m1 and m2 are 1 or more. The material has the effect of emitting light having a very high brightness and in which its color changes variously in accordance with the number of m1, m2 and n.

A twelfth aspect of the present invention is a luminous material using a molecular compound having the following molecular structure:

[Compound 23]

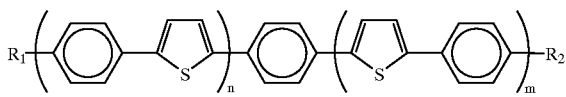

wherein R1 and R2 each independently represents any one of hydrogen, an alkyl group, an alkenyl group and a halogen; and n and m are 1 or more. The material has the effect of emitting light having a far higher brightness by alternate arrangement of the thiophene rings and the benzene rings, and in which its color changes variously in accordance with the number of m and n.

A thirteenth aspect of the present invention is a lumuinous material using a molecular compound having the following molecular structure:

[Compound 24]

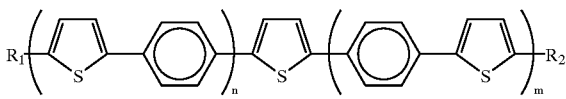

wherein R1 and R2 each independently represents any one of hydrogen, an alkyl group, an alkenyl group and a halogen; and n and m are 1 or more. The material has the effect of emitting light having a far higher brightness by alternate arrangement of the thiophene rings and the benzene rings, and in which its color changes variously in accordance with the number of m and n.

A fourteenth aspect of the present invention is a luminous material using a molecular compound having the following molecular structure:

[Compound 25]

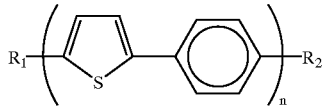

wherein R1 and R2 each independently represents any one of hydrogen, an alkyl group, an alkenyl group and a halogen; and n is 1 or more. The material has the effect of emitting light having a far higher brightness by alternate arrangement of the thiophene ring (s) and the benzene ring (s), and in which its color changes variously in accordance with the number of n.

A fifteenth aspect of the present invention is a luminous material using a molecular compound having the following molecular structure:

[Compound 26]

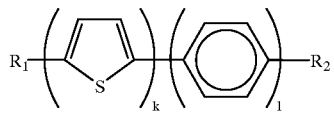

wherein R1 and R2 each independently represents any one of hydrogen, an alkyl group, an alkenyl group and a halogen; and at least one of k and l is 2 or more. The material has the effect of emitting light having a very high brightness and in which its color changes variously in accordance with the number of k and l.

A sixteenth aspect of the present invention is a molecular compound having the following molecular structure.

[Compound 27]

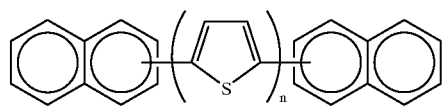

wherein n is 1 or more.

The compound has the effect of realizing a luminous material which emits light having a very high brightness and in which its color changes variously in accordance with the number of n.

A seventeenth aspect of the present invention is a luminous material comprising a molecular compound having a molecular structure wherein a thiophene ring and a naphthalene ring are directly bonded each other. The material has the effect of giving a luminous color having a high brightness.

An eighteenth aspect of the present invention is a luminous material according to the seventeenth aspect, wherein the number of the thiophene ring and the naphthalene ring and the bonding order of the rings are changed to control its luminous color. The material has the effect that its luminous color is controlled and light having various color tones are emitted with a high brightness.

A nineteenth aspect of the present invention is a luminous compound using a molecular compound having the following molecular structure.

[Compound 28]

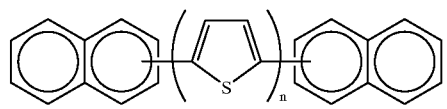

wherein n is 1 or more.

The compound has the effect that light having a very high brightness can be emitted and its color changes variously in accordance with the number of n.

A twentieth aspect of the present invention is a luminous material comprising any combination of two or more kinds of the luminous materials according to the 7th–15th aspects, and the 17th–19th aspects. The material has the effect of emitting light having various color tones with a high brightness.

A twenty first aspect of the present invention is an organic electroluminesence element having at least a luminous layer sandwiched between a pair of electrodes, wherein the luminous layer comprises one or more molecular compounds according to the 1st–6th and 16th aspects. The element has the effect that multicolor is made easy and the luminous efficiency thereof is improved by using as the luminous layer a material the color tone of which is easily changed and the fluorescence yield of which is high.

A twenty second aspect of the present invention is an organic electroluminesence element having at least a luminous layer sandwiched between a pair of electrodes, wherein the luminous layer comprises a complex of one or more molecular compounds according to the 1st–6th and the 16th aspects, and a molecular compound other than these molecular compounds. The element has the effect of realizing more various luminous colors and simultaneously keeping an action having high efficiency and stability for a long time. The above-mentioned complex includes a mixture of two or more kinds of molecular compounds, and complexes wherein a molecular compound as a host is doped with another kind of molecular structure, complexes wherein layers comprising such a molecular compound are appropriately stacked.

By such structures and aspects, the present invention provides a series of molecular compounds making it possible to easily cope with both control of their luminous color and realization of emitting light having a high brightness efficiently; and luminous materials using a series of molecular compound. These molecular compounds include entirely new compounds and compounds which have already been known but whose effect of coping with both of the control of their luminous color and highly efficient and bright luminescence has not been recognized up to the present.

All of the molecular compounds according to the present invention have a feature that a thiophene ring and a benzene ring are directly bonded to each other and their luminous colors can easily be changed by the number of these rings and the bonding order thereof. As a result, the luminous materials using these molecular compounds are used to realize luminescence having wide colors from purple to red highly efficiently.

Therefore, the present invention has advantages that it is possible to provide new functional molecular compounds which can be used in the chemical industry and the electronic industry, and luminous materials using them to have high efficiency and brightness.

The present specification describes, as a thiophene ring and a benzene ring in the present invention, only 2-substituted, 2,5-di-substituted, and 1,4-di-substituted rings. Of course, however, it is possible to use thiophen rings and benzene rings having a substituent at other positions than the above. As a naphthalene ring, a 1-substituted ring can be effectively used as well as a 2-substituted ring described in the specification.

Generally, the present invention includes compounds wherein different two or more kinds aromatic rings are appropriately linked in a linear form; and luminous materials comprising them. The aromatic rings include benzene, naphthalene, anthracene, azulene, phenanthrene, thiophene, pyrrole, and furan rings; cyclic compounds comprising similar aromatic compounds; and hetero-cyclic compounds.

In the case that the molecular compounds according to the present invention are used as luminous materials, their solid forms can include powder, a thin film, and a form wherein the molecular compound is dispersed into a suitable matrix. Their liquid forms can include various forms such as a solution and a suspension. In all of the cases, the molecular compounds exhibit excellent effects as a luminous material.

The present invention will be in detail described hereinafter, referring to attached drawings.

DESCRIPTION OF THE PREFERRED EMBODIMENT

The electroluminesence element of the present invention will be described hereinafter, referring to the attached drawings.

Figure 1:
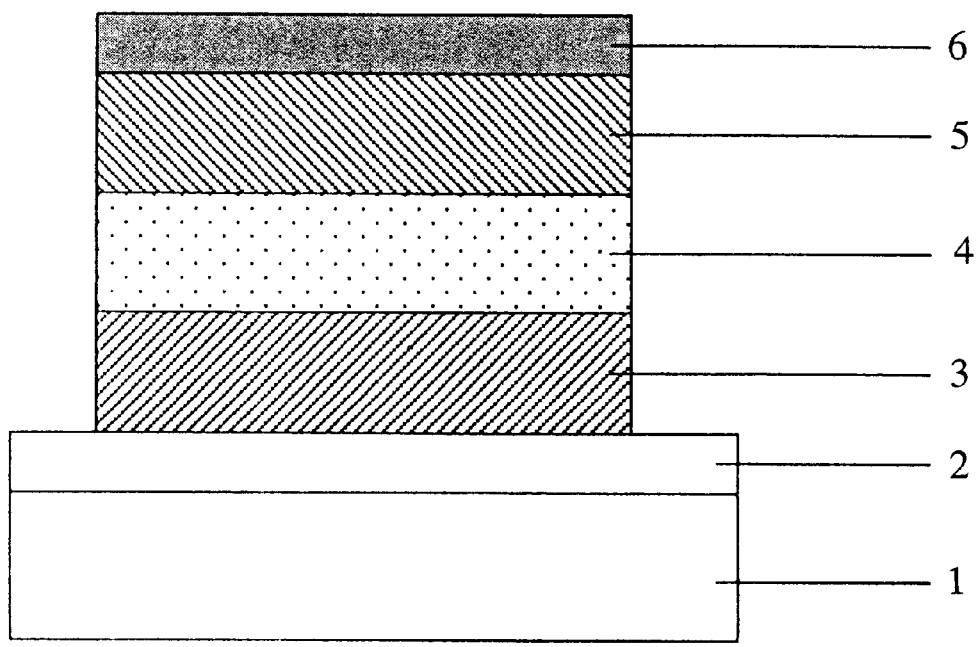
FIG. 1 is a cross section illustrating a structural outline of an organic luminous element of the present invention.

FIG. 1 is a cross section illustrating a structural outline of an organic luminous element of the present invention The organic electroluminesence element illustrated in FIG. 1 is an element wherein a positive electrode (transparent electrode) 2 is formed on a glass substrate 1 and a hole transport layer 3, a luminous layer 4, an electron transport 5 and an upper electrode 6 are stacked in this order on the positive electrode 2. The luminous layer 4 can function as the hole transport layer 3 or the electron transport layer 5. Other layers can be inserted therebetween as the occasion demands Specific examples thereof include a hole injection layer inserted between the transparent layer 2 and the hole transport layer 3, a hole blocking layer inserted between the luminous layer 4 and the electron transport layer 5, and an electron injection layer inserted between the electron transport layer 5 and the negative electrode (the upper electrode) 6. Moreover, the luminous layer 4 is made up to a lamination structure to cause its plural luminous layers to emit simultaneously.

The luminous layer 4 is usually formed by vacuum evaporation based on resistance-heating. The luminous layer 4 may be made by depositing a luminous molecule dispersed into a polymer such as polycarbonate by spin coating. The thickness of the luminous layer is usually 10 nm or more, and is preferably selected from the range of 20–300 nm.

The molecular compounds corresponding to the 1st–6th embodiments and the 16th embodiment can be used as materials for making the luminous layer. They may be used singly or in a combination of thereof. It is also easy to use them with other known molecular compounds which do not correspond to the 1st–6th embodiments or the 16th embodiment. Thus, various luminous colors, such as white, can be obtained.

The molecular compound of the present invention may be dispersed into a suitable host material to use a dopant. Examples of the host material in this case include quinolinol metal complexes; oxazol, thiazol, imidazol, styryl, distyrylarylene, coumalin, butadiene and triphenyl amine derivatives. The concentration of the dopant is preferably from 0.1 to 10 mol %.

The molecular compound of the present invention, as a host material, is doped with other luminous materials to make a luminous layer. Examples of the dopant in this state include quinacridone, coumalin, styryl and quinolinol derivatives; and condensed polycyclic aromatic compounds. The concentration of the dopant, which varies according to its kind, is preferably from 0.05 to 5 mol %.

The following will describe processes for synthesizing new molecular compounds according to Examples of the present invention, and evaluation of these molecular compounds as luminous materials, referring to the attached drawings.

EXAMPLE 1

As a first Example of the present invention, a process for synthesizing a molecular compound having a phenyl group at both terminals thereof (referred to compound A hereinafter) will be described. This molecular compound is a new compound having the following molecular structure.

[Compound 29]

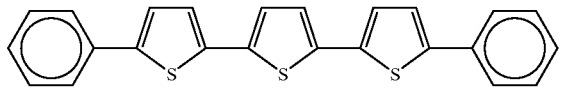

In order to produce this molecular compound, into a 500 mL three-neck flask was first added 4.62 g (0.19 mol) of magnesium, and then the three-neck flask was subjected to vacuum suction, and intensely heated with a heat gun to be dried. Next, 100 mL of anhydrous diethyl ether (made by Wako Pure Chemicals Industries, Ltd.) was added thereto and then the solution was sufficiently stirred. To this solution was dropwise added 50 mL of an anhydrous diethyl ether solution into which 29.8 g (0.19 mol) of bromobenzene (made by Tokyo Kasei Co., Ltd.) was dissolved through a dropping funnel.

The resultant was further stirred. After the reaction solution started to be refluxed by generated heat based on reaction of magnesium with bromobenzene, the solution was cooled with ice to keep the rate of the reaction of magnesium appropriate.

After it was confirmed that all amounts of magnesium were reacted to finish the synthesis of a Grignard reagent, 542 mg (1 mmol) of 1,3-bis (diphenylphosphino) propanenickel (II) chloride (Strem company) was added to the reaction solution. Thereafter, 50 mL of a diethyl ether solution into which 26.1 g (0.16 mol) of 2-bromothiophene was dissolved was added dropwise to the reaction solution through a dropping funnel. Furthermore, the reaction solution was continuously stirred one day and night, and subsequently the reaction solution was heated with an oil bath for 6 hours to be refluxed. Thereafter, the solution was cooled with an ice bath, and 100 mL of 2 N hydrochloric acid was dropwise added thereto through a dropping funnel to quench a non-reacted Grignard reagent, thereby finishing the synthesis reaction. This solution was in sequence washed with water, a saturated solution of sodium hydrogencarbonate and water and dried with anhydrous calcium chloride.

This was filtered and then diethyl ether was evaporated off with a rotary evaporator to obtain 26.9 g of solid 2-phenylthiophene.

Next, 3.21 g (20 mmol) of the thus synthesized 2-phenylthiophene was dissolved into 20 mL of methanol, and then to this solution was added a solution wherein 3.92 g (22 mmol) of N-bromosuccinimide (Wako Pure Chemicals Industries, Ltd.) was dissolved into 40 mL of methanol, to produce a white precipitation of 2-phenyl-5-bromothiophene immediately. This reaction solution was put into a refrigerator to ensure the production of the precipitation. This precipitation was filtered and then was sufficiently washed with a great deal of a mixture solution of equivalent amounts of water and methanol. The resultant was dried one day and night to obtain a white crystal (2.4 g) of 2-phenyl-5-bromothiophene.

Next, 239.1 mg (1 mmol) of a sample was separated from the crystal of 2-phenyl-5-bromothiophene and this sample, together with 24.3 mg of magnesium, was added to a 30 mL one-neck eggplant type flask. The flask was sucked and mildly heated with a heat gun to be dried, and then 10 mL of diethyl ether was added to this so as to dissolve 2-phenyl-5-bromothiophene therein. The solution was stirred to prepare a Grignard reagent.

After it was confirmed that all amounts of magnesium were reacted, 10 mg of 1,3-bis (diphenylphosphio) propanenickel (II) chloride were added to the reaction solution. To this solution was incorporated a solution wherein 134.4 mg (0.4 mmol) of 2,5-diiodothiophene (made by Aldrich Company) dried beforehand was dissolved into 5 mL of anhydrous diethyl ether.

Immediately after the incorporation, a yellow precipitation was produced which was 5,5"-diphenyl-2,2':5', 2"-terthiophene (compound A). This was stirred one day and night and then was refluxed for 6 hours. Next, this was cooled over a water bath, and then 1 mL of 2 N hydrochloric acid was added thereto so as to quench a non-reacted Grignard reagent. This was filtered and the resultant precipitation was washed with acetone to obtain 140 mg of a yellow crystal of 5,5"-diphenyl-2,2':5', 2"-terthiophene (compound A).

Figure 2:
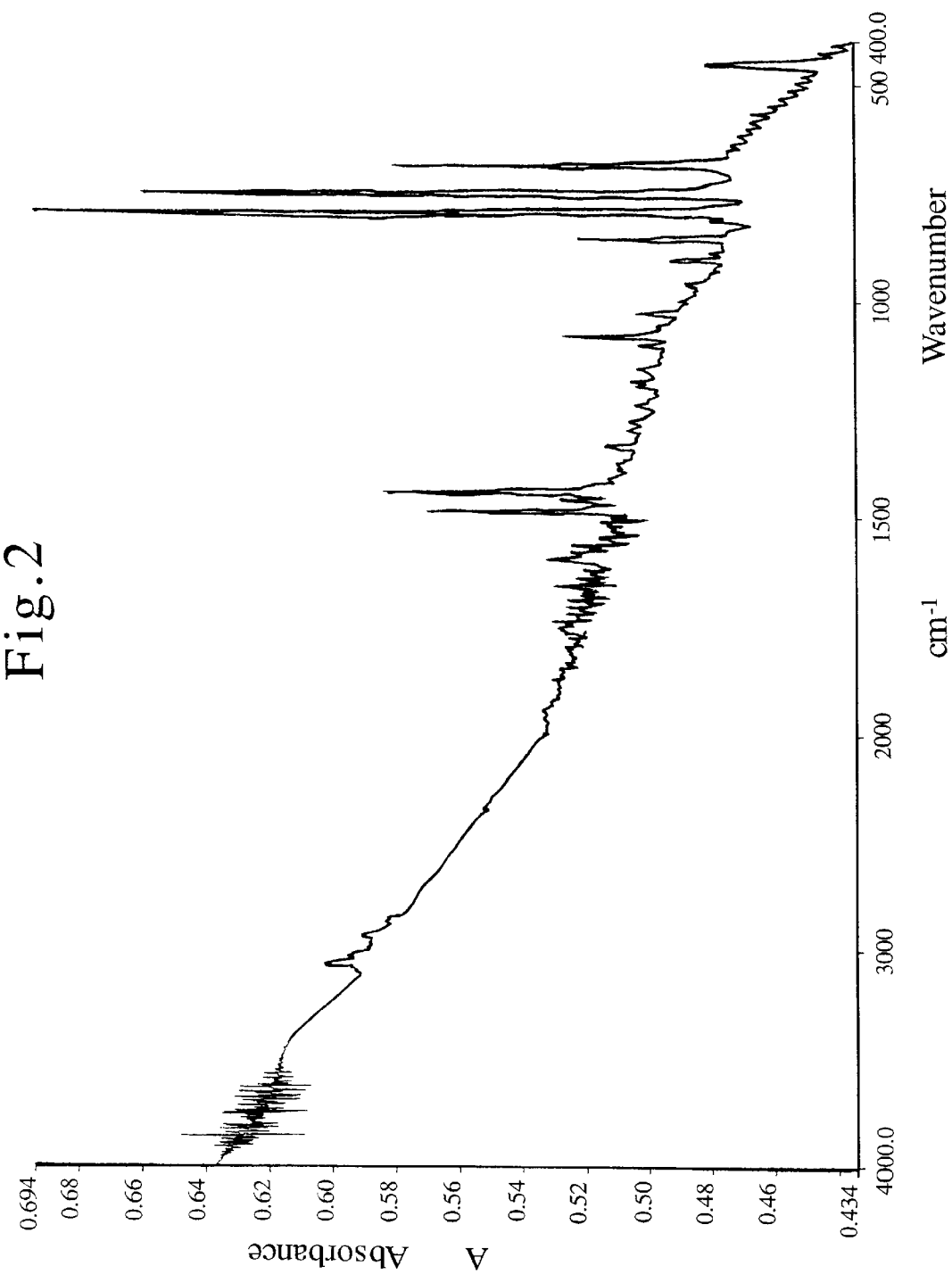
FIG. 2 is a view showing an infrared spectrum of a molecular compound (compound A) according to a first Example of the present invention.

FIG. 2 shows an infrared spectrum of the compound A. In FIG. 2, peaks at 1439.6 cm$^{-1}$ and 790.7 cm$^{-1}$ were assigned to ring stretching vibration and CH out-of-plane bending vibration of the 2,5-di-substituted thiophene ring. A peak at 1483.8 cm$^{-1}$ was assigned to ring stretching vibration of the mono-substituted benzene ring, and peaks at 750.2 cm$^{-1}$ and 683.8 cm$^{-1}$ were assigned to CH out-of-plane bending vibration of the same mono-substituted benzene ring.

In the present Example and the following Examples, their spectra were measured by using an infrared spectroscopic photometer (Perkin Elmer System 2000FT-IR) about tablets obtained by separating several solid pieces from the samples obtained by recrystallizing crystals from a suitable solvent, and cracking and dispersing the pieces into potassium bromide, and press-molding the resultant.

EXAMPLE 2

As a second Example of the present invention, a process for synthesizing another molecular compound having a phenyl group at both terminals thereof (referred to compound B hereinafter) will be described. This molecular compound is a new compound having the following molecular structure.

[Compound 30]

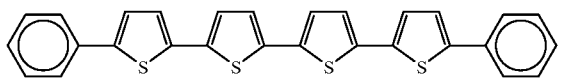

In order to produce this molecular compound, 239.1 mg (1 mmol) of a sample were separated from the 2-phenyl-5-bromothiophene synthesized in Example 1, and this sample, together with 24.3 mg of magnesium, was put in a 30 mL one-neck eggplant type flask in the same way as in Example 1. The one-neck flask was subjected to vacuum suction, and mildly heated with a heat gun to be dried. Next, 10 mL of anhydrous diethyl ether was added thereto and then 2-phenyl-5-bromothiophene was dissolved therein. This solution was stirred to prepare a Grignard reagent.

After it was confirmed that all amounts of magnesium were reacted, nitrogen gas was blown into the flask to evaporate diethyl ether. Next, 10 mL of anisole(made by Aldrich company) was added thereto, and then 10 mg of 1,3-bis(diphenylphosphino)propanenickel (II) chloride was added thereto. Further, 167 mg (0.4 mmol) of solid 5,5'-diiodo-2,2'-terthiophene which was beforehand prepared and then vacuum-dried, was added thereto.

This reaction solution was stirred one day and night, and then was heated at 100° C. for 6 hours. Next, the solution was cooled over an ice bath, and 1 mL of 2 N hydrochloric acid was added thereto to quench a non-reacted Grignard reagent. This solution was filtered and then the precipitation was sufficiently washed with acetone to obtain 20 mg of an orange crystal of 5,5'"-diphenyl-2,2':5', 2":5",2'"-quaterthiophene (compound B).

The process for preparing 5,5'-diiodo-2,2'-bithiophen was as follows. Into 100 mL of methanol was dissolved 1.663 g (10 mmol) of bithiophen (made by Aldrich company), and then 50 mL of a methanol solution into which 4.95 g (22 mmol) of N-iodosuccinimide (made by Aldrich company) was dissolved was added to the above-mentioned solution. While this solution was stirred, 1.87 mL (22 mmol) of concentrated hydrochloric acid was dropwise and slowly added to this solution. Thus, a white precipitation was produced and the reaction solution became viscous. Therefore, 50 mL of methanol was added thereto, and then the solution was continuously stirred for 2 hours, and subsequently 3.06 mL (22 mmol) of an aqueous ammonia solution was added thereto so as to finish the reaction. This was filtered and the resultant precipitation was washed with a great deal of water and vacuum-dried one day and night to obtain 2.0 g of a colorless crystal of 5,5'-diiodo-2,2'-bithiophene.

Figure 3:
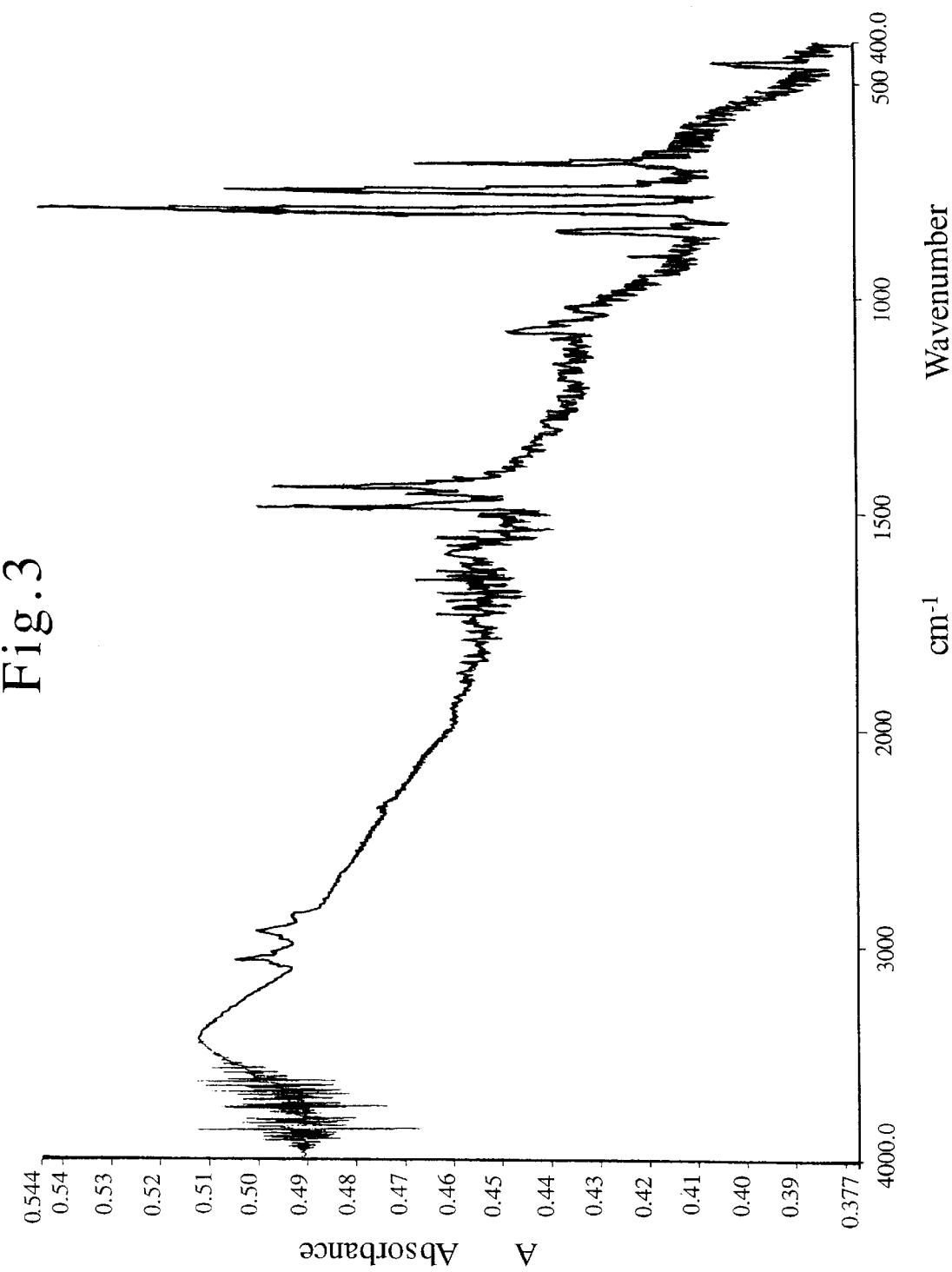
FIG. 3 is a view showing an infrared spectrum of a molecular compound (compound B) according to a second Example of the present invention.

FIG. 3 shows an infrared spectrum of the compound B. In FIG. 3, peaks at 1439.6 cm$^{-1}$ and 790.7 cm$^{-1}$ were assigned to ring stretching vibration and CH out-of-plane bending vibration of the 2,5-di-substituted thiophene ring. A peak at 1487.5 cm$^{-1}$ was assigned to ring stretching vibration of the mono-substituted benzene ring, and peaks at 746.5 cm$^{-1}$ and 683.8 cm$^{-1}$ were assigned to CH out-of-plane bending vibration of the same mono-substituted benzene ring.

EXAMPLE 3

As a third Example of the present invention, a process for synthesizing still another molecular compound having a phenyl group at both terminals thereof (referred to compound C hereinafter) will be described. This molecular compound is a new compound having the following molecular structure.

[Compound 31]

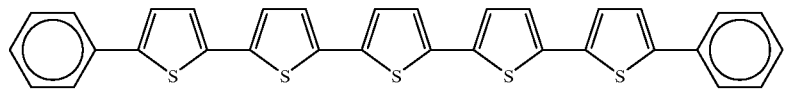

In order to produce this molecular compound, 1.60 g (10 mmol) of a sample was separated from the 2-phenylthiophene synthesized in Example 1, and this sample, together with 4.50 g (20 mmol) of N-iodosuccinimide (made by Aldrich company), was put in a conical flask. To this solution was added 10 mL of methanol. Furthermore, 1.14 mL (20 mmol) of acetic acid was added to this solution. The solution was stirred for some time to produce a white crystal. This was put into a refrigerator to ensure the production of the precipitation. This precipitation was filtered and then was sufficiently washed with a great deal of a mixture solution of equivalent amounts of water and methanol. The resultant was dried one day and night to obtain a white crystal (2.5 g) of 2-phenyl-5-iodothiophene.

Next, 286.1 mg (1 mmol) of a sample was separated from the crystal of 2-phenyl-5-iodothiophene and this sample, together with 24.3 mg (1 mmol) of magnesium, was added to a 30 mL one-neck eggplant type flask. The flask was subjected to vacuum suction and mildly heated with a heat gun to be dried, and then 10 mL of anhydrous diethyl ether was added to this so as to dissolve 2-phenyl-5-iodothiophene therein. The solution was stirred to prepare a Grignard reagent.

After it was confirmed that all amounts of magnesium were reacted, nitrogen gas was blown into the flask to evaporate diethyl ether. Next, 10 mL of anisole was added thereto, and then 10 mg of 1,3-bis(diphenylphosphino)propanenickel (II) chloride was added thereto. Further, 200 mg (0.4 mmol) of solid 5,5"-diiodo-2,2':5',2"-terthiophene, which was beforehand prepared and then vacuum-dried, was added thereto.

This reaction solution was stirred one day and night, and subsequently the reaction solution was heated at 100° C. for 6 hours. Next, the solution was cooled over an ice bath, and 1 mL of 2 N hydrochloric acid was added thereto to quench a non-reacted Grignard reagent. This solution was filtered and then the precipitation was sufficiently washed with acetone to obtain 10 mg of an reddish orange crystal of 5,5''''-diphenyl-2,2':5', 2'':5''',2''':5''',2''''-quinquethiophene (compound C).

The process for preparing 5,5''-diiodo-2,2':5', 2''-terthiophene was as follows. Into 20 mL of methanol were dissolved 248.4 mg (1 mmol) of terthiophene(made by Aldrich company) and 495 mg (2.2 mmol) of N-iodosuccinimide (made by Aldrich company). Four drops (about 120 μL) of acetic acid were added to this solution to produce a yellowish green precipitation after some time. Therefore, this was put into a refrigerator to ensure the production of the precipitation.

This precipitation was filtered, sufficiently washed with a great deal of methanol, and dried one day and night to obtain a yellowish green crystal (440 mg) of 5,5''-diiodo- 2,2':5', 2''-terthiophene.

Figure 4:
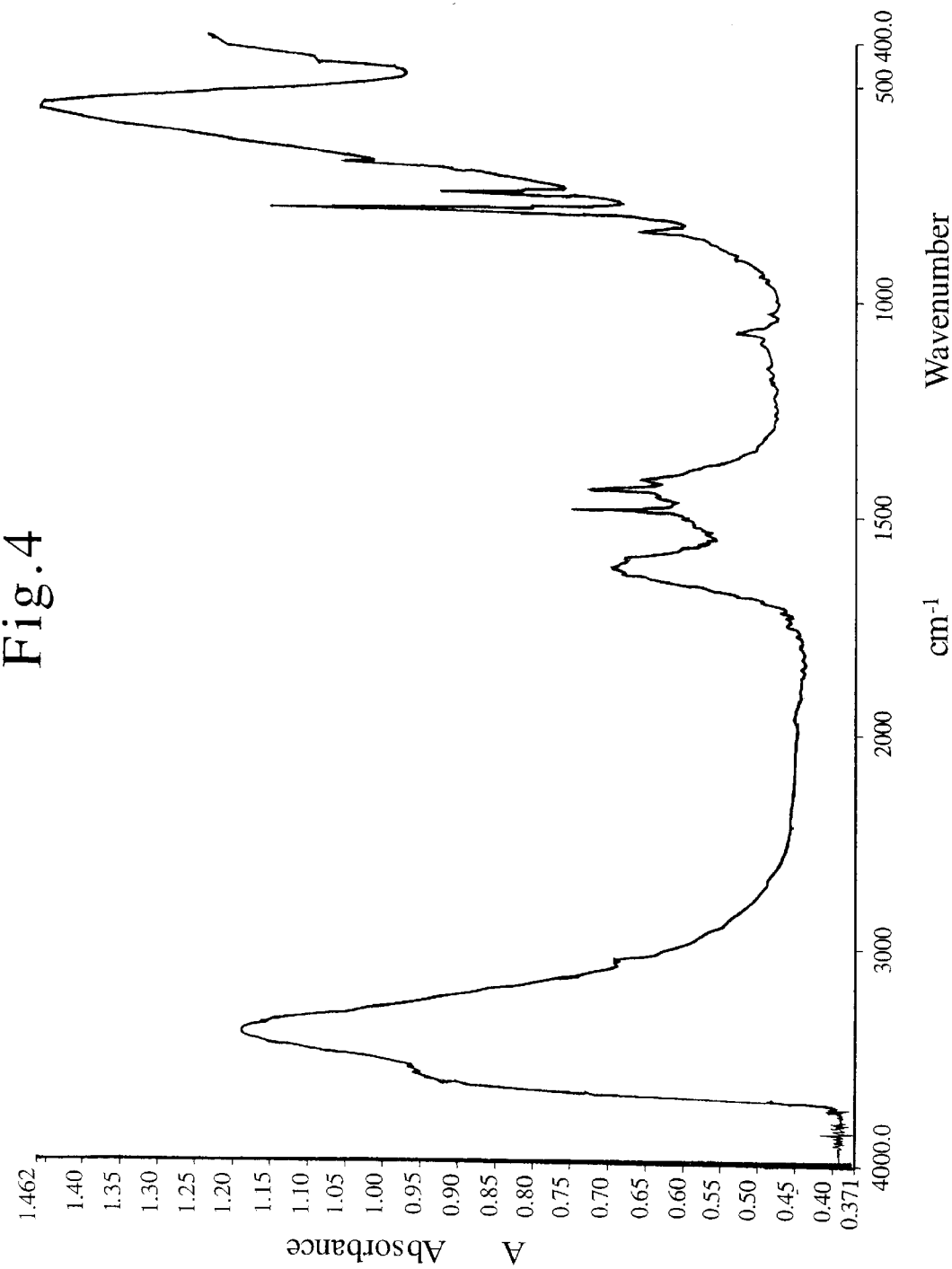
FIG. 4 is a view showing an infrared spectrum of a molecular compound (compound C) according to a third Example of the present invention.

FIG. 4 shows an infrared spectrum of the compound C. In FIG. 4, peaks at 1439.6 cm$^{-1}$ and 790.7 cm were assigned to ring stretching vibration and CH out-of-plane bending vibration of the 2,5-di-substituted thiophene ring. A peak at 1487.5 cm$^{-1}$ was assigned to ring stretching vibration of the mono-substituted benzene ring, and peaks at 750.2 cm$^{-1}$ and 683.8 cm$^{-1}$ were assigned to CH out-of-plane bending vibration of the same mono-substituted benzene ring.

Concerning the compound C synthesized in the present Example, any solvent for dissolving this was not able to be found. Thus, a spectrum measurement was carried out through no recrystallization. It appears that roundish and intense peaks at about 3000 cm$^{-1}$, 1500 cm$^{-1}$ and 500 cm$^{-1}$ in FIG. 4 were generated by the compound C doped with an ionic material taken into the sample in the synthesizing process.

EXAMPLE 4

As a forth Example of the present invention, a process for synthesizing a molecular compound having a biphenylyl group at both terminals thereof (referred to compound D hereinafter) will be described. This molecular compound is a new compound having the following molecular structure.

[Compound 32]

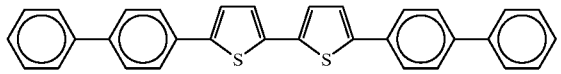

In order to produce this molecular compound, into a 300 mL three-neck flask was first added 1.10 g (45.3 mmol) of magnesium, and then the three-neck flask was subjected to vacuum suction, and intensely heated with a heat gun to be dried. Next, 50 mL of anhydrous diethyl ether was added thereto and then the solution was sufficiently stirred. To this solution was dropwise added 30 mL of an anhydrous diethyl ether solution into which 9.51 g (45.3 mmol) of 2-iodothiophene (made by Aldrich company) was dissolved, through a dropping funnel.

The resultant was further stirred. After the reaction solution started to be refluxed by generated heat based on reaction of magnesium with 2-iodothiophene, the solution was cooled with ice to keep the rate of the reaction of magnesium appropriate.

After it was confirmed that all amounts of magnesium were reacted to finish the synthesis of a Grignard reagent, 130 mg (0.24 mmol) of 1,3-bis(diphenylphosphino) propanenickel (II) chloride was added to the reaction solution. Next, 8.45 g (36.2 mmol) of 4-bromobiphenyl (made by Tokyo Kasei Co., Ltd.), which was beforehand vacuum-dried, was added in a solid form. Furthermore, the reaction solution was continuously stirred one day and night, and subsequently the reaction solution was heated over an oil bath for 8 hours to be refluxed.

Thereafter, the solution was cooled with an ice bath, and 25 mL of 2 N hydrochloric acid was dropwise added thereto through a dropping funnel to quench a non-reacted Grignard reagent, thereby finishing the synthesis reaction. The produced precipitation was filtered, and then sufficiently washed with a great deal of a mixture solution of water and methanol in equivalent amounts. Thereafter, the precipitation was dried one day and night to obtain 1.2 g of 2-(4-biphenylyl) thiopene (referred to as compound E hereinafter) as an intermediate. This molecular compound is a molecular compound having the following molecular structure.

[Compound 33]

Next, 472.7 mg (2 mmol) of a sample were separated from the thus synthesized 2-(4-biphenylyl) thiophene crystal, and then this sample was dissolved into 20 mL of acetone, and then to this solution was added a solution wherein 391.6 mg (2.2 mmol) of N-bromosuccinimide was dissolved into 10 mL of methanol, to produce a White crystal of 2-(4-biphenylyl)-5-bromothiophene after some time. This reaction solution was put into a refrigerator to ensure the production of the precipitation. This precipitation was filtered and then was sufficiently washed with a great deal of a mixture solution of eqivalent amounts of water and methanol. The resultant was dried one day and night to obtain a white crystal (375 mg) of 2-(4-biphenylyl)-5-bromothiophene.

Furthermore, into a 30 mL one-neck eggplant type flask were added 130.8 mg (0.2 mmol) of bis(triphenylphosphine) nickel (II) dichloride (Tokyo Kasei Co., Ltd.), 738.7 mg (2 mmol) of tetrabutylammonium iodide (Tokyo Kasei Co., Ltd.) and 261.6 mg (4 mmol) of zinc powder (Wako Pure Chemicals Industries, Ltd.), and the flask was subjected to vacuum suction, and the mixture, was mildly heated with a heat gun to be dried. To this mixture was added 10 ml of anhydrous tetrahydrofuran (made by Dohjin Kagaku company, a grade for synthesizing a nucleic acid), and then the solution was stirred so that the color of the solution changed into reddish brown.

To this solution was added 157.6 mg (0.5 mol) of the thus obtained 2-(4-biphenylyl)-5-bromothiophene in a solid form. The solution was heated at 100° C. for about 4 hours and simultaneously stirred. Thereafter, the reaction solution was cooled to room temperature and then 4 mL of 2 N hydrochloric acid was added thereto. The solution was sufficiently stirred to finish the reaction. This was washed with a great deal of methylene chloride to obtain 27 mg of a yellow crystal of 5,5'-bis(4-biphenylyl)-2,2'-bithiophene (compound D).

Figure 5:
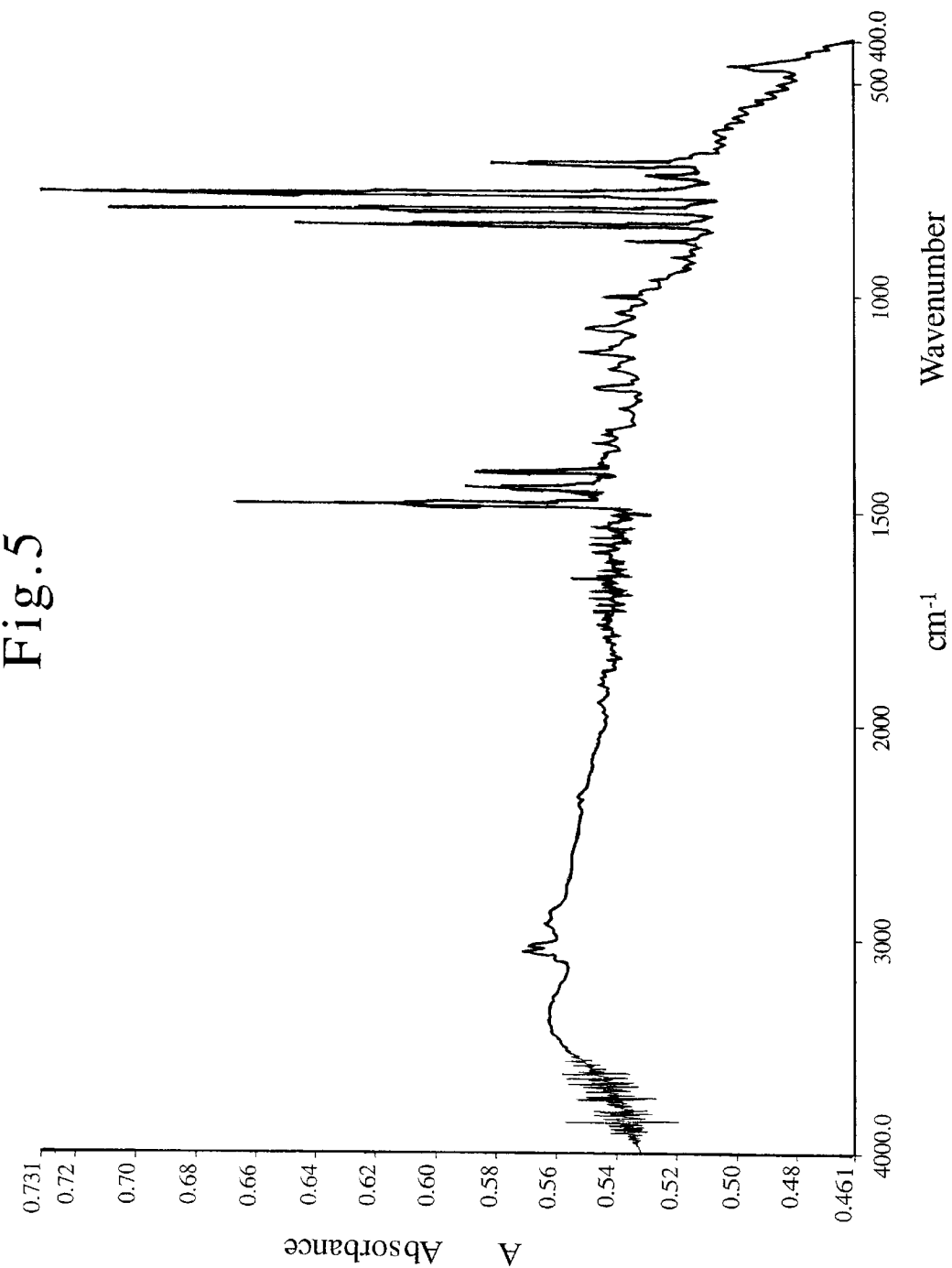
FIG. 5 is a view showing an infrared spectrum of a molecular compound (compound D) according to a forth Example of the present invention.

FIG. 5 shows an infrared spectrum of the compound D. In FIG. 5, peaks at 1443.3 cm$^{-1}$ and 794.4 cm$^{-1}$ were assigned to ring stretching vibration and CH out-of-plane bending vibration of the 2,5-di-substituted thiophene ring. Peaks at 1480.1 cm$^{-1}$ and 1406.4 cm$^{-1}$ were assigned to ring stretching vibration of the mono-substituted benzene ring and the 1,4-di-substituted ring in 4-biphenylyl group, respectively, and peaks at 757.6 cm$^{-1}$ and 687.5 cm$^{-1}$ were assigned to CH out-of-plane bending vibration of the mono-substituted benzene ring in the same 4-biphenylyl group. A peak at 831.3 cm$^{-1}$ was assigned to CH out-of-plane bending vibration of the 1,4-di-substituted benzene ring in the 4-biphenylyl group.

Figure 6:
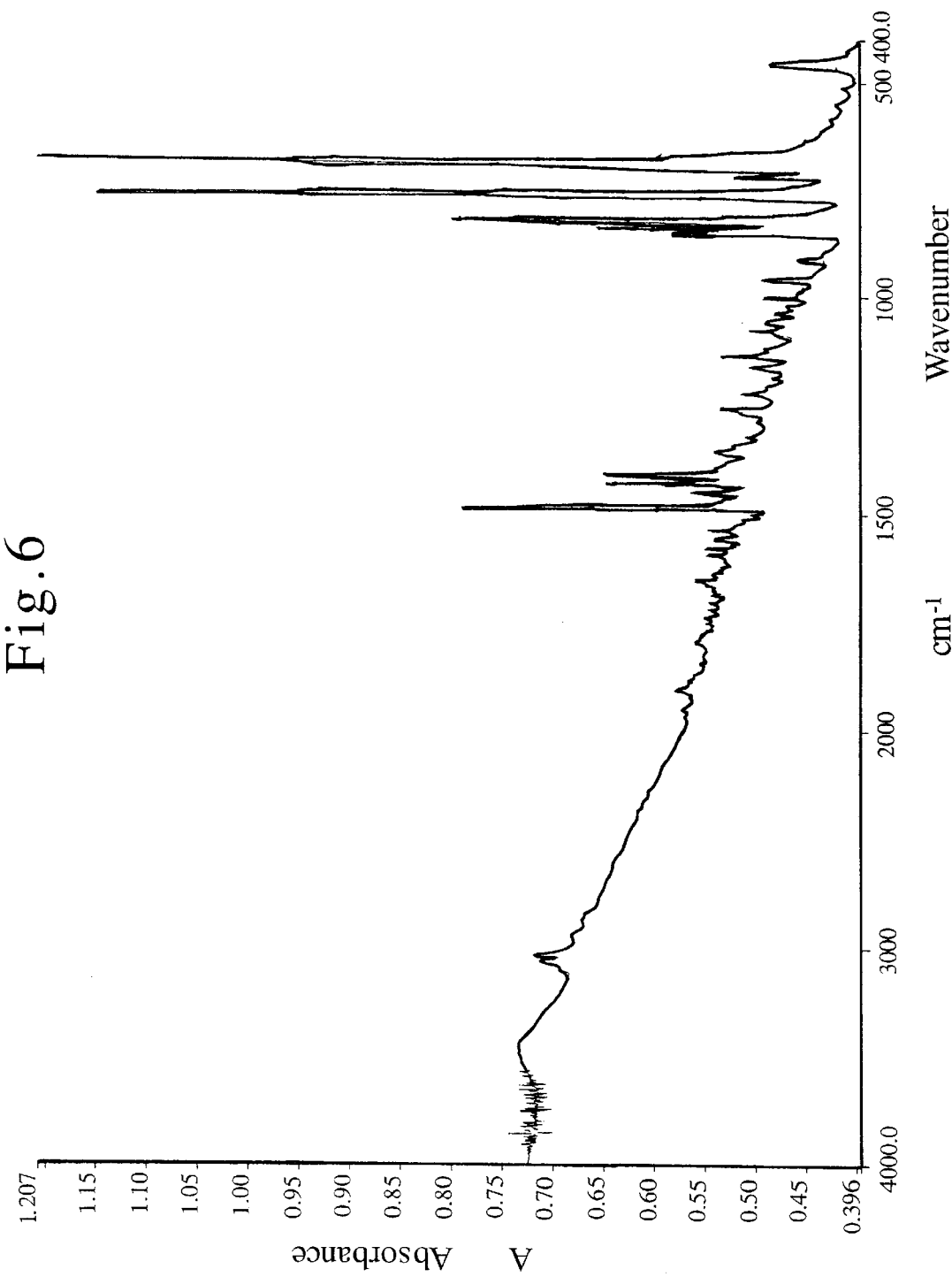
FIG. 6 is a view showing an infrared spectrum of a molecular compound (compound E) according to a forth Example of the present invention.

FIG. 6 shows an infrared spectrum of the compound E. In FIG. 6, a peak at 1424.8 cm$^{-1}$ was assigned to ring stretching vibration of the 2-substituted thiophene ring. Peaks at 1483.8 cm$^{-1}$ and 1406.4 cm$^{-1}$ were assigned to ring stretching vibration of the mono-substituted benzene ring and the 1,4-di-substituted ring in the 4-biphenylyl group, respectively, and peaks at 761.2 cm$^{-1}$ and 683.8 cm$^{-1}$ were assigned to CH out-of-plane bending vibration of the mono-substituted benzene ring in the same 4-biphenylyl group. A peak at 820.2 cm$^{-1}$ was assigned to CH out-of-plane bending vibration of the 1,4-di-substituted benzene ring in the 4-biphenylyl group.

EXAMPLE 5

The molecular compound of the present invention includes a compound wherein a thiophene ring and a benzene ring are alternately arranged. As a fifth embodiment, one compound (referred to as compound F hereinafter) among them will be described. This molecular compound is a new compound having the following molecular structure.

[Compound 34]

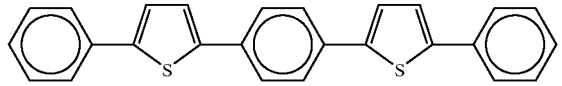

In order to produce this molecular compound, 286.1 mg (1 mmol) of a sample was separated from 2-phenyl-5-iodothiophene synthesized in Example 3, and this sample, together with 24.3 mg (1 mmol), was added to a 30 mL one-neck eggplant type flask. The flask was subjected to vacuum suction and mildly heated with a heat gun to be dried, and then 10 mL of anhydrous diethyl ether were added to this so as to dissolve 2-phenyl-5-iodothiophene therein. The solution was stirred to prepare a Grignard reagent.

After it was confirmed that all amounts of magnesium were reacted, 5 mg of 1,3-bis (diphenylphosphino) propanenickel (II) chloride was added to the reaction solution. Next, 132 mg (0.4 mmol) of solid 1,4-diiodobenzene, which was beforehand vacuum-dried, was added thereto. This reaction solution was continuously stirred one day and night, and subsequently the reaction solution was heated over an oil bath for 8 hours to be refluxed.

Thereafter, the solution was cooled with an ice bath, and 1 mL of 2 N hydrochloric acid was added thereto through a dropping funnel to quench a non-reacted Grignard reagent. Thus, the synthesis reaction was finished. This solution was filtered and then the precipitation was sufficiently washed with acetone and dried one day and night to obtain 36 mg of a yellow crystal of 1,4-bis(5-phenylthiophene-2-yl) benzene (compound F).

Figure 7:
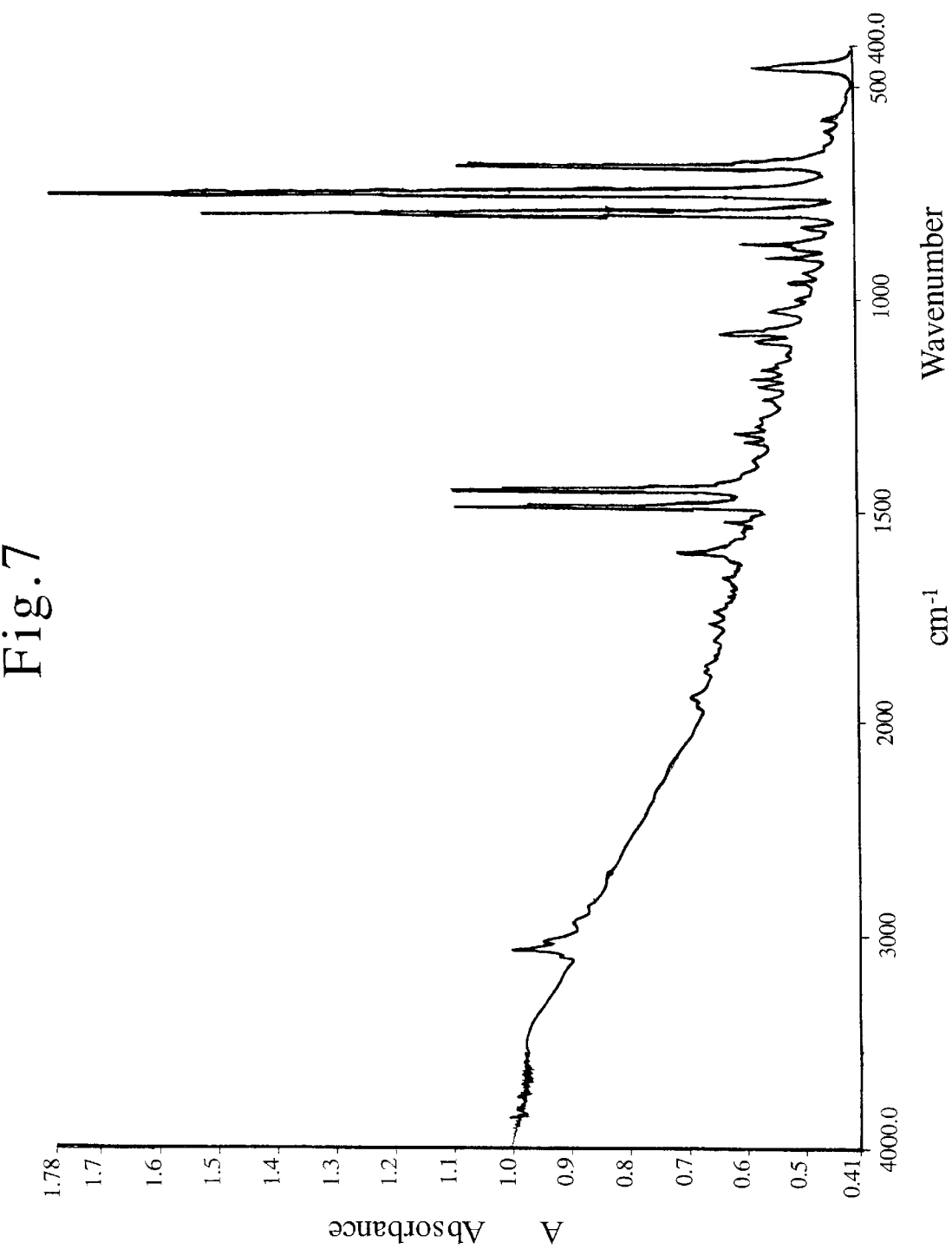
FIG. 7 is a view showing an infrared spectrum of a molecular compound (compound F) according to a fifth Example of the present invention.

FIG. 7 shows an infrared spectrum of the compound F. In FIG. 7, peaks at 1443.3 cm$^{-1}$ and 794.4 cm$^{-1}$ were assigned to ring stretching vibration and CH out-of-plane bending vibration of the 2,5-di-substituted thiophene ring, respectively. A peak at 1483.8 cm$^{-1}$ was assigned to ring stretching vibration of the mono-substituted benzene ring, and peaks at 750.2 cm$^{-1}$ and 683.8 cm$^{-1}$ were assigned to CH out-of-plane bending vibration of the same mono-substituted benzene ring. A peak at 831.3 cm$^{-1}$ was assigned to CH out-of-plane bending vibration of the 1,4-di-substituted benzene ring.

EXAMPLE 6

The molecular compound of the present invention includes an asymmetric compound wherein thiophene rings and benzene rings are bonded. As a sixth embodiment, one compound (referred to as compound G hereinafter) among them will be described. This molecular compound is a new compound having the following molecular structure.

[Compound 35]

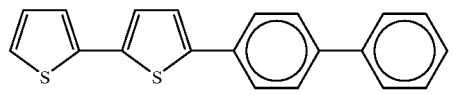

In order to produce this molecular compound, 31.5 mg (0.1 mmol) of a sample was separated from 2-(4-biphenylyl)-5-bromothiophene synthesized in Example 4, and this sample, together with 51.2 mg (0.4 mmol) of 2-thiopheneboronic acid (made by Aldrich company), was added to a conical flask. To this was added 10 mL of benzene, and the solution was heated for dissolution. Nitrogen was then bubbled for 30 minutes in order to remove dissolved oxygen.

Thereafter, 11.6 mg (10 μmol) of tetrakis (triphenylphosphine)palladium (0) (made by Aldrich company) was added thereto, and then 5 mL of an aqueous solution of 106 mg (1 mmol) of sodium carbonate (made by Wako Pure Chemicals Industries, Ltd.) was further added thereto. The solution was refluxed one day and night while the reactor was kept in the state that air was substituted by nitrogen.

Thereafter, the reactor was cooled to room temperature, and then the reaction solution was quenched with 0.1 mL of aqueous hydrogen peroxide solution. This was washed with water, and then benzene was evaporated off with a rotary evaporator to yield 20 mg of a solid of 5-(4-biphenylyl)-2, 2'-bithiophene (compounds G).

Figure 8:
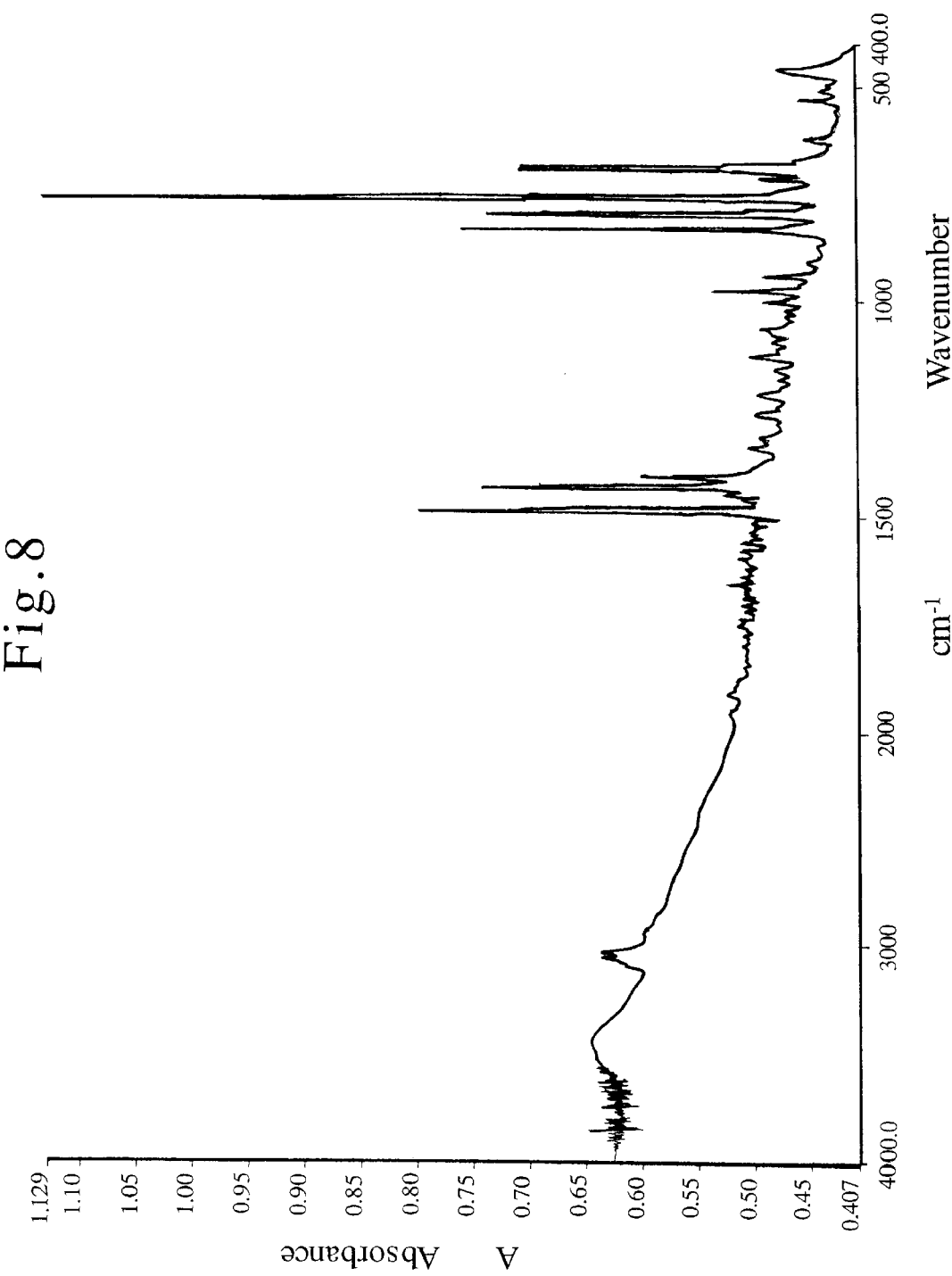
FIG. 8 is a view showing an infrared spectrum of a molecular compound (compound G) according to a sixth Example of the present invention.

FIG. 8 shows an infrared spectrum of the compound G. In FIG. 8, a peak at 1428.5 cm$^{-1}$ was assigned to ring stretching vibration of the 2-substituted thiophene ring. Peaks at 1483.8 cm$^{-1}$ and 1406.4 cm$^{-1}$ were assigned to ring stretching vibration of the mono-substituted benzene ring and the 1,4-di-substituted benzene ring in the 4-biphenylyl group, respectively. Peaks at 757.6 cm$^{-1}$ and 687.5 cm$^{-1}$ were assigned to CH out-of-plane bending vibration of the mono-substituted benzene ring in the same 4-biphenyl group. A peak at 831.3 cm$^{-1}$ was assigned to CH out-of-plane bending vibration of the 1,4-di-substituted benzene ring in the 4-biphenylyl group.

EXAMPLE 7

As a seventh embodiment, a process for synthesizing another compound (referred to as compound H hereinafter) of the asymmetric compound wherein a thiophene ring and a benzene ring are bonded will be described. This molecular compound is a new compound having the following molecular structure.

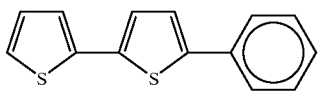
[Compound 36]

In order to produce this molecular compound, a Grignard reagent was prepared from 150.6 mg (6.2 mmol) of magnesium and 1.30 g (6.2 mmol) of 2-iodothiophene in the same way as in Example 4.

To this reaction solution was added 20 mg of 1,3-bis (diphenylphosphino)propanenickel (II) chloride, and then 1.185 g (4.96 mmol) of 2-phenyl-5-bromothiophene which was beforehand vacuum-dried was added in a solid form to the above-mentioned Grignard reagent solution. The solution was continuously stirred one day and night, and subsequently the reaction solution was heated over an oil bath for 4 hours to be refluxed.

Thereafter, the solution was cooled with ice, and then 4 mL of 2N hydrochloric acid was dropwise added thereto through a dropping funnel to quench a non-reacted Grignard reagent, thereby finishing the synthesis reaction. This solution was washed with water, an aqueous saturated sodium hydrogencarobonate, and water in this order, and was then dried with anhydrous calcium chloride. This was filtered and then diethyl ether was evaporated off with a rotary evaporator to obtain 1.0 g of a solid of 5-phenyl-2,2'-bithiophene (compound H).

Figure 9:
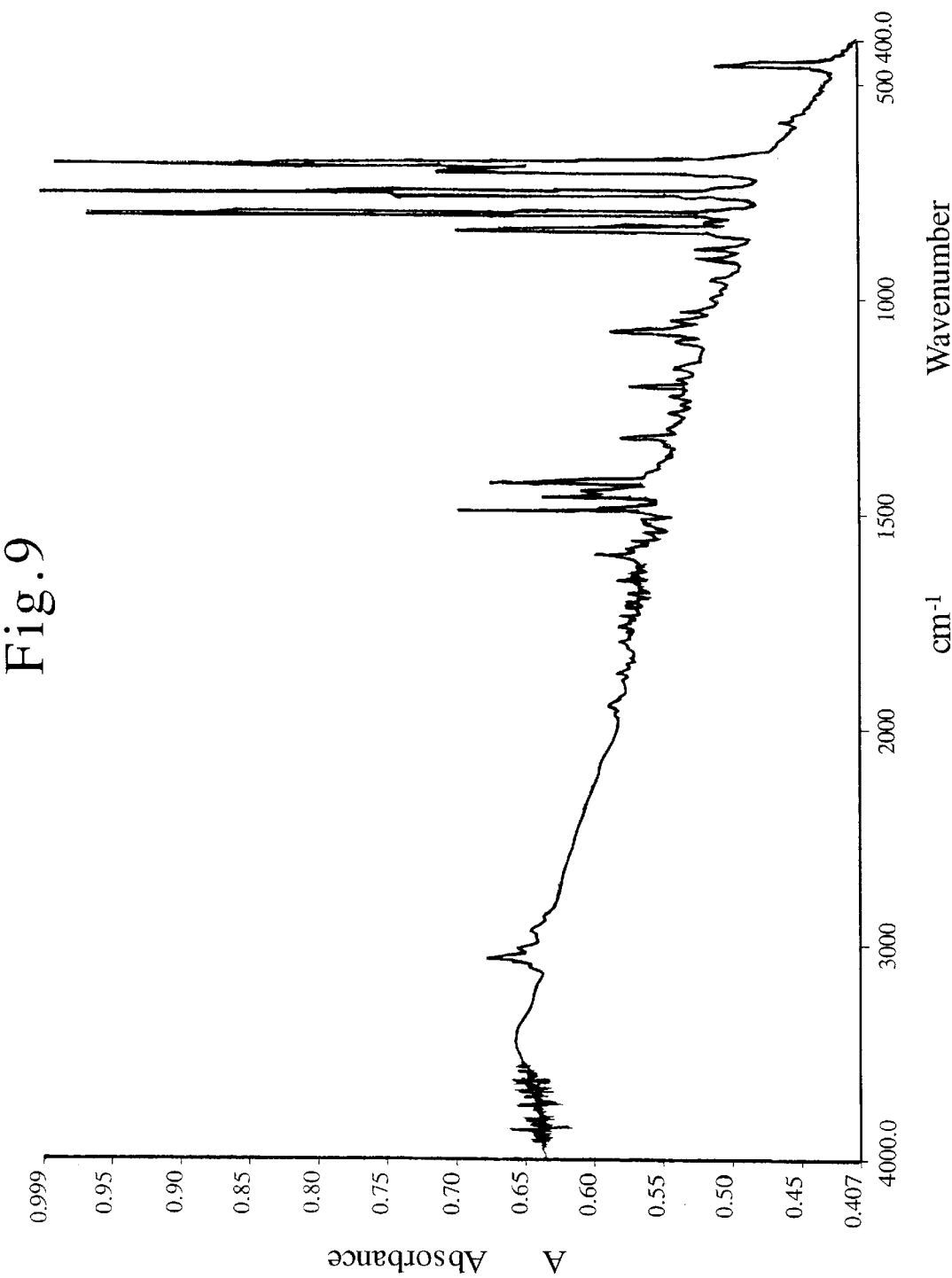
FIG. 9 is a view showing an infrared spectrum of a molecular compound (compound H) according to a seventh Example of the present invention.

FIG. 9 shows an infrared spectrum of the compound H. In FIG. 9, a peak at 1421.1 $cm^{-1}$ was assigned to ring stretching vibration of the 2-substituted thiophen ring. Peaks at 1443.3 $cm^{-1}$ and 798.1 $cm^{-1}$ were assigned to ring stretching vibration and CH out-of-plane bending vibration of the 2,5-di-substituted thiophene, respectively. A peak at 1491.2 $cm^{-1}$ was assigned to ring stretching vibration of the mono-substituted benzene ring. Peaks at 753.9 $cm^{-1}$ and 683.8 $cm^{-1}$ were assigned to CH out-of-plane bending vibration of the same mono-substituted benzene ring.

EXAMPLE 8

The present Example will describe the fact that the compounds described in the above-mentioned Examples are useful as luminous materials.

Several solid pieces of samples were taken out with a spatula from the above-mentioned Examples. The samples were put into sample tubes and then the tubes are sealed. These sample tubes were irradiated with ultraviolet rays (wavelength: 365 nm) from an ultraviolet lamp, and then the color tone and brightness of fluorescence emitted from the samples were measured with eyes. The results are shown in Table 1.

TABLE 1

Color tone and brightness of fluorescence (No.1)

| Compound | Color tone | Brightness |
|---|---|---|
| Compound of Example 1 (Compound A) | Yellowish orange | Very intence |
| Compound of Example 2 (Compound B) | Reddish orange | Very intence |
| Compound of Example 3 (Compound C) | Red | Intense |

TABLE 1-continued

Color tone and brightness of fluorescence (No.1)

| Compound | Color tone | Brightness |
|---|---|---|
| Compound of Example 4 (Compound D) | Yellow | Very intence |
| Compound of Example 4 (Compound E) | Purple | Intense |
| Compound of Example 5 (Compound F) | Yellow | Very intence |
| Compound of Example 6 (Compound G) | Yellowish green | Intense |
| Compound of Example 7 (Compound H) | Green | Very intense |

Known comparative examples include oligothiophene compounds described in, for example, J. Mater. Chem. 1. 835 (1991), S. Hotta and K. Waragai. Solid samples of them were also put into sample tubes and then the sample tubes were sealed. These sample tubes were irradiated with ultraviolet rays (wavelength: 365 nm) from an ultraviolet lamp, and then the color tone and brightness of fluorescence emitted from the samples were measured with eyes. The observed results of these oligothiophene compounds are shown in Table 2.

The compounds A, B and C correspond to compounds represented by the general formula:

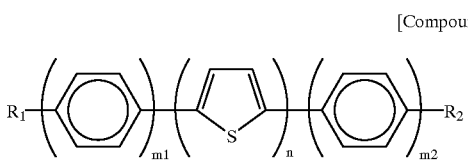
[Compound 37]

wherein m1=m2=1, and n is 3,4 and 5, respectively. These compounds are molecular compounds according to claim 2. It can be understood that their color tones change variously in accordance with the number of n.

TABLE 2

Color tone and brightness of fluorescence (Known compounds)

| Compound | Color tone | Brightness |
|---|---|---|
| 5.5"-Dimethyl-2,2':5',2"'-terthiophene | Green | Faint |
| 5.5"'-Dimethyl-2,2':5',2":5",2"'-quaterthiophene | Yellow | Faint |
| 5,5""-Dimethyl-2,2':5',2":5",2"':5"',2""-quinquethiophene | Orange | Very faint |
| 5,5"""-Dimethyl-2,2':5',2":5",2"':5"', 2"":5"",2""'-sexithiophene | Red | Very faint |

As a result from comparison of the above-mentioned two tables, it can be understood that the luminous bodies using the oligothiophene can give change in the color tone to some extent, but their brightness is poorer than that of Examples of the present invention.

EXAMPLE 9

The following will describe an outline of a process for synthesizing compounds that have already been known as compounds and have utility as luminous materials, which has not been reported or known; and their characteristics as luminous materials.

i) 2,5-Diphenylthiophene

This compound is a known compound having the following molecular structure.

[Compound 38]

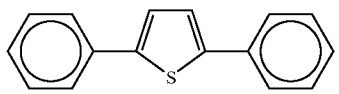

In order to produce this molecular compound, a Grignard reagent was prepared from 298 mg (1.90 mmol) of bromobenzene and 46.2 mg (1.90 mmol) of magnesium in the same way as in Example 1. To this reaction solution was added 20 mg of 1,3-bis(diphenylphosphino)propanenickel (II) chloride, and then 227 mg (0.95 mmol) of 2-phenyl-5-bromothiophene, which was prepared in Example 1 and beforehand vacuum-dried, were added in a solid form to the above-mentioned Grignard reagent solution. The reaction solution was continuously stirred one day and night and then heated over an oil bath for 4 hours to be refluxed. This reaction solution was treated in the same way in Example 1 to obtain 60 mg of the target compound (colorless crystal).

ii) 5,5'-Diphenyl-2,2'-bithiophene

This compound is a known compound having the following molecular structure.

[Compound 39]

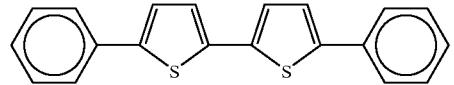

In order to produce this molecular compound, 24.3 mg (1 mmol) of magnesium was put to a 30 mL one-neck eggplant type flask, and then the flask was intensely heated to be vacuum-dried. At the same, time, 239.1 mg (1 mmol) of 2-phenyl-5-bromothiophene prepared in Example 1 was mildly heated in another 30 mL one-neck eggplant type flask to be vacuum-dried. Next, this 2-phenyl-5-bromothiophene was dissolved into 15 mL of anhydrous diethyl ether, and then this was poured into the flask in which magnesium was put, and then the solution was stirred to prepare a Grignard reagent.

After it was confirmed that all amounts of magnesium disappeared, 10 mg of 1,3-bis(diphenylphosphino) propanenickel (II) chloride was added thereto. Furthermore, 191.3 mg (0.8 mmol) of 2-phenyl-5-bromothiophene, which was beforehand vacuum-sucked, was added in a solid form to the above-mentioned Grignard reagent solution. The solution was continuously stirred one day and night, and then was heated over an oil bath for 4 hours to be refluxed. The resultant lightly yellow precipitation was filtered and washed a great deal of methanol to obtain 175 mg of the target compound.

iii) 1,4-Bis(2-thienyl)benzene

This compound is a known compound having the following. molecular structure.

[Compound 40]

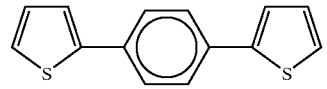

In order to produce this molecular compound, a Grignard reagent was prepared from 761 mg (3.62 mmol) of 2-iodethiophen and 88 mg (3.62 mmol) of magnesium in the same manner as in Example 4. To this was added 30 mL of 1,3-bis(diphenylphosphino)propranenickel (II) chloride, and then 478 mg (1.45 mmol) of 1,4-iodobenzene (made by Aldrich company), which was beforehand vacuum-dried, was added in a solid form to the solution of the Grignard reagent. Furthermore, the reaction solution was continuously stirred and subsequently was heated over an oil bath for 4 hours to be refluxed. The resultant precipitation was filtered and washed with a great deal of cold methanol to obtain 60 mg of the target compound (colorless crystal).

iv) 4,4'-Bis(2-thienyl)biphenyl

This compound is a known compound having the following molecular structure.

[Compound 41]

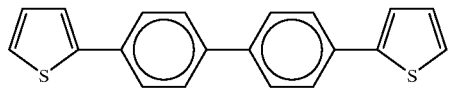

In order to produce this molecular compound, a Grignard reagent was prepared from 8.675 g (41.3 mmol) of 2-iodothiophene and 1.004 g (41.3 mmol) of magnesium in the same manner in Example 4. To this reaction solution was added 320 mg of 1,3-bis(diphenylphosphino)propranenickel (II) chloride, and then 6.50 g (16.0 mmol) of 4,4'-diiodobiphenyl (made by Tokyo Kasei Co., Ltd.), which was beforehand vacuum-dried, was added in a solid form to the solution of the Grignard reagent. Furthermore, the reaction solution was continuously stirred, and subsequently was heated over an oil bath for 8 hours to be refluxed. The resultant precipitation was filtered and washed with a great deal of methanol and acetone to obtain 4.3 g of the target compound (lightly yellow crystal).

Next, concerning these compounds, their fluorescent properties were evaluated in the same manner as in Example 8. The results are shown in Table 3.

TABLE 3

Color tone and brightness of fluorescence (Compounds for new use)

| Compound | Color tone | Brightness |
|---|---|---|
| Compound of Example i) | Blue | Very intense |
| Compound of Example ii) | Yellowish green | Very intense |
| Compound of Example iii) | Greenish blue | Very intense |
| Compound of Example iv) | Blue green | Very intense |

Regarding, for example, the compounds iii) and iv), their synthesis processes are described in J. Chem. Soc., Chem. Commu., 1987, 764, T. Mitsuhara, K. Kaeriyama and S. Tanaka, and the like documents. However, these descriptions relate to application thereof as a conductive material. The descriptions are entirely different from the present invention in uses and objects.

Examples of the present invention describe only the fluorescent properties based on irradiation with ultraviolet rays from an ultraviolet lamp, but does not refer to electroluminescent properties. However, the fluorescent properties and the electroluminescent properties are commom in most of luminous spectra and mechanism. Descriptions related thereto are included in Appl. Phys. Lett. 58, 1982 (1991), D. Braun and A. J. Heeger, Appl. Phys. 66, 109 (1997), Tetsuo Tsutsui, and the like. For this reason, evaluation about fluorescent properties by irradiation with light is a simple and practical index for evaluating electroluminescent properties. Besides, it appears that the molecular compounds and the luminous materials of the present invention can be validly used as raw materials for colorant laser.

In the above-mentioned Examples, only the compounds wherein their thiophene ring and benzene ring do not have any substituent were handled. Compounds wherein these are appropriately substituted by an alkyl or alkenyl group, or halogen can be validly used. As understood from Table 1 and 3, the luminous materials of the present invention make it possible to emit light having various color tones and high brightness by changing the total number of the thiophene rings and the benzene rings, and the bonding order thereof. It was recognized that, in particular, the molecular compounds wherein the thiophene rings and the benzenens are alternately arranged, for example, the molecular compound described in Example 5 give far more intense brightness than the molecular compounds having other bonding orders of the thiophene rings and the benzene rings, rather than they generally give very intense brightness.

About the color tones described in Tables 1 and 3, even the color tones described by the same wording, for example, "yellow" and "yellowish green", give subtle change and difference in actual color tones in accordance with the difference in the molecular compounds. When the plural kinds of the molecular compounds of the present invention were combined to observe color tones and brightness of fluorescence emitted from the samples by irradiating the samples with ultraviolet rays from an ultraviolet lamp, it was also proved that the resultant color tones were mixed in accordance with the luminous properties of the respective molecular compounds to cause a subtle change in the color tones. Thus, the present invention provides excellent luminous materials which can freely realize desired color tones.

Since the molecular compounds and the luminous materials of the present invention have a molecular skeleton comprising stable thiophene and benzene rings, they are excellent in environment-resistance and the like. This is also one of important effects and advantages of the present invention.

EXAMPLE 10

As a tenth Example of the present invention, a process for synthesizing a molecular compound having a phenyl group at both terminals thereof (referred to compound I hereinafter) will be described. This molecular compound is a new compound having the following molecular structure.

[Compound 42]

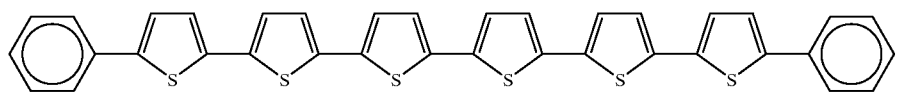

In order to produce this molecular compound, 4.29 g (25 mmol) of bithiophene (made by Aldrich company) were dissolved into 40 mL of methanol, and then 40 mL of a methanol solution into which 5.92 g (25 mmol) of N-iodosuccinimide (made by Aldrich company) was dissolved was added to the above-mentioned solution. When the solution was stirred, 1.43 mL (25 mmol) of acetic acid was dropwise and slowly added thereto. After some time, a white precipitation was produced. This was put: into a refrigerator and allowed to stand for 4 hours to finish the production of the precipitation. The white precipitation was removed by filtration, and 80 ml of water and 120 ml of diethyl ether were added to the filtrate. This was in sequence washed with water, a 10% potassium hydroxide solution, and water, and then dried with anhydrous calcium chloride. This was filtrated and then diethyl ether was evaporated off with a rotary evaporator to obtain 3.7 g of 5-iodo-2,2'-bithiophene.

Next, the 2-phenyl-5-iodothiophene crystal obtained in the manner described in Example 3, 583.9 mg (2.04 mmol) and 49.6 mg of magnesium were added to a 30 mL one-neck eggplant type flask, and then the flask was vacuum-sucked in the same manner as in Example 3, and mildly heated with a heat gun to be dried. To this was added 10 mL of anhydrous diethyl ether for dissolution of 2-phenyl-5-iodothiophene. The solution was stirred to prepare a Grignard reagent.

After it was confirmed that all amounts of magnesium were reacted, 20 mg of 1,3-bis(diphenylphosphino) propanenickel (II) chloride was added thereto. Furthermore, 397.5 mg (1.36 mmol) of 5-iodo-2,2'-bithiophene, which was beforehand prepared and dissolved into 5 mL of anhydrous diethyl ether, was added thereto.

This was stirred one day and night, and subsequently was refluxed for 6 hours. Thereafter, the solution was cooled with a water bath, and 1 mL of 2 N hydrochloric acid was added thereto to quench a non-reacted Grignard reagent. The resultant precipitation was filtered and sufficiently washed with methanol to obtain 420 mg of a yellow crystal of 5-phenyl-2,2':5',2"-terthiophene (which may be referred to as compound J hereinafter) This compound is a new compound having the following molecular structure.

[Compound 43]

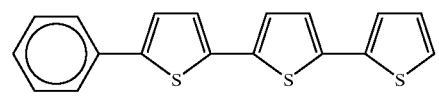

5-Phenyl-2,2':5',2"-terthiophene(the compound J) was used to carry out the following synthesis. That is, 194.7 mg (0.6 mmol) of 5-phenyl-2,2':5',2"-terthiophene synthesized as above and 177.6 mg (0.75 mmol) of N-iodosuccinimide (made by Aldrich company) were dissolved into 20 mL of methylene chloride, and then 43 μL of acetic acid Was added thereto. The solution was stirred over an ice bath for 2 hours. This was filtered and sufficiently washed with methanol to obtain 146 mg (0.32 mmol) of a golden crystal of 5-phenyl-5"-iodo-2,2':5',2"-terthiophene.

Next, to a 30 mL one-neck eggplant type flask were added 84.8 mg (0.128 mmol) of bis(triphenylphosphine)nickel (II) dichloride (made by Tokyo Kasei Co., Ltd.), 478.9 mg (1.28 mmol) of tetrabutylammonium iodide (Tokyo Kasei Co., Ltd.) and 169.6 mg (2.56 mmol) of zinc powder, and the flask was vacuum-sucked and mildly heated with a heat gun to be dried. To this was added 15 mL of tetrahydrofuran (made by Dohjin Kagaku company, a grade for synthesizing a nucleic acid), and then the solution was stirred so that the color of the solution changed to red brown.

To this solution was added 146 mg (0.32 mmol) of the 5-phenyl-5"-iodo-2,2':5',2"-terthiophene crystal obtained above, in a solid form. The solution was stirred for 7 hours while being heated at 100° C. Thereafter, the reaction solution was cooled to room temperature and then 3 mL of 2 N hydrochloric acid was added thereto. The solution was sufficiently stirred to finish the reaction. This was washed with a great deal of methylene chloride to obtain 20 mg of a red crystal of 5,5""'-diphenyl-2,2':5',2":5",2"':5"',2"":5"", 2""'-sexithiophene (compound I).

Figure 10:
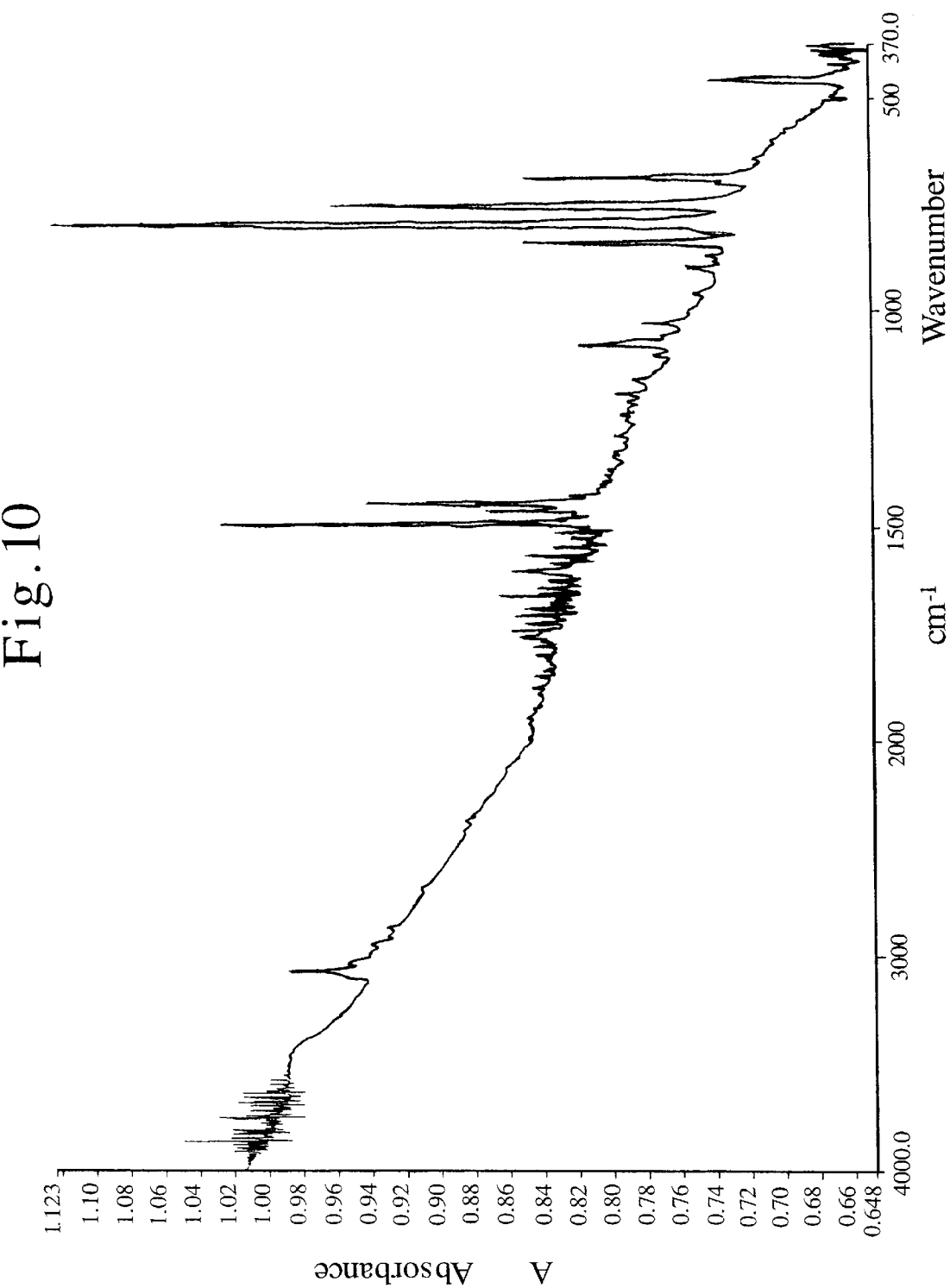
FIG. 10 is a view showing an infrared spectrum of a molecular compound (compound I) according to a tenth Example of the present invention.

FIG. 10 shows an infrared spectrum of the compound I. In FIG. 10, peaks at 1441.8 $cm^{-1}$ and 792.5 $cm^{-1}$ were assigned to ring stretching vibration and CH out-of-plane bending vibration of the 2,5-di-substituted thiophene ring, respectively. A peak at 1488.0 $cm^{-1}$ was assigned to ring stretching vibration of the mono-substituted benzene ring, and peaks at 750.3 $cm^{-1}$ and 686.0 $cm^{-1}$ were assigned to CH out-of-plane bending vibration of the same mono-substituted benzene ring.

Figure 11:
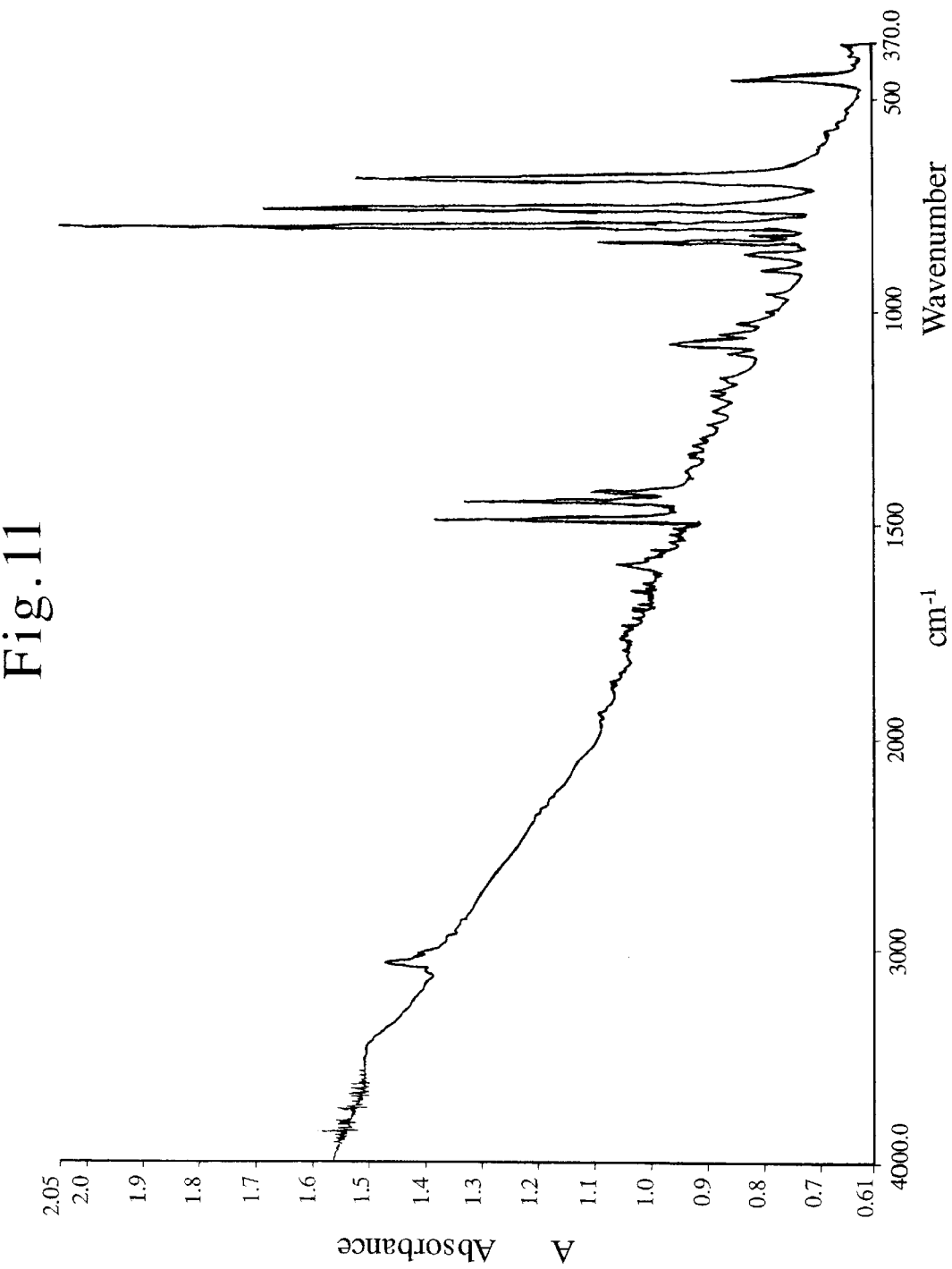
FIG. 11 is a view showing an infrared spectrum of a molecular compound (compound J) according to a tenth Example of the present invention.

FIG. 11 shows an infrared spectrum of the compound J. In FIG. 11, peaks at 1447.0 $cm^{-1}$ and 1424.7 $cm^{-1}$ were assigned to ring stretching vibration of the 2,5-di-substituted thiophene ring and 2-substituted thiophene ring, respectively. A peak at 1488.9 $cm^{-1}$ was assigned to ring stretching vibration of the mono-substituted benzene ring, and peaks at 751.7 $cm^{-1}$ and 684.7 $cm^{-1}$ were assigned to CH out-of-plane bending vibration of the same mono-substituted benzene ring.

reaction solution was quenched with 1 mL of an aqueous hydrogen peroxide solution. The reaction solution was filtered and then the resultant lightly yellow precipitation was sufficiently washed with methanol to obtain 393 mg of a solid of 2,5-bis(4-biphenylyl) thiophene (compound K).

Figure 12:
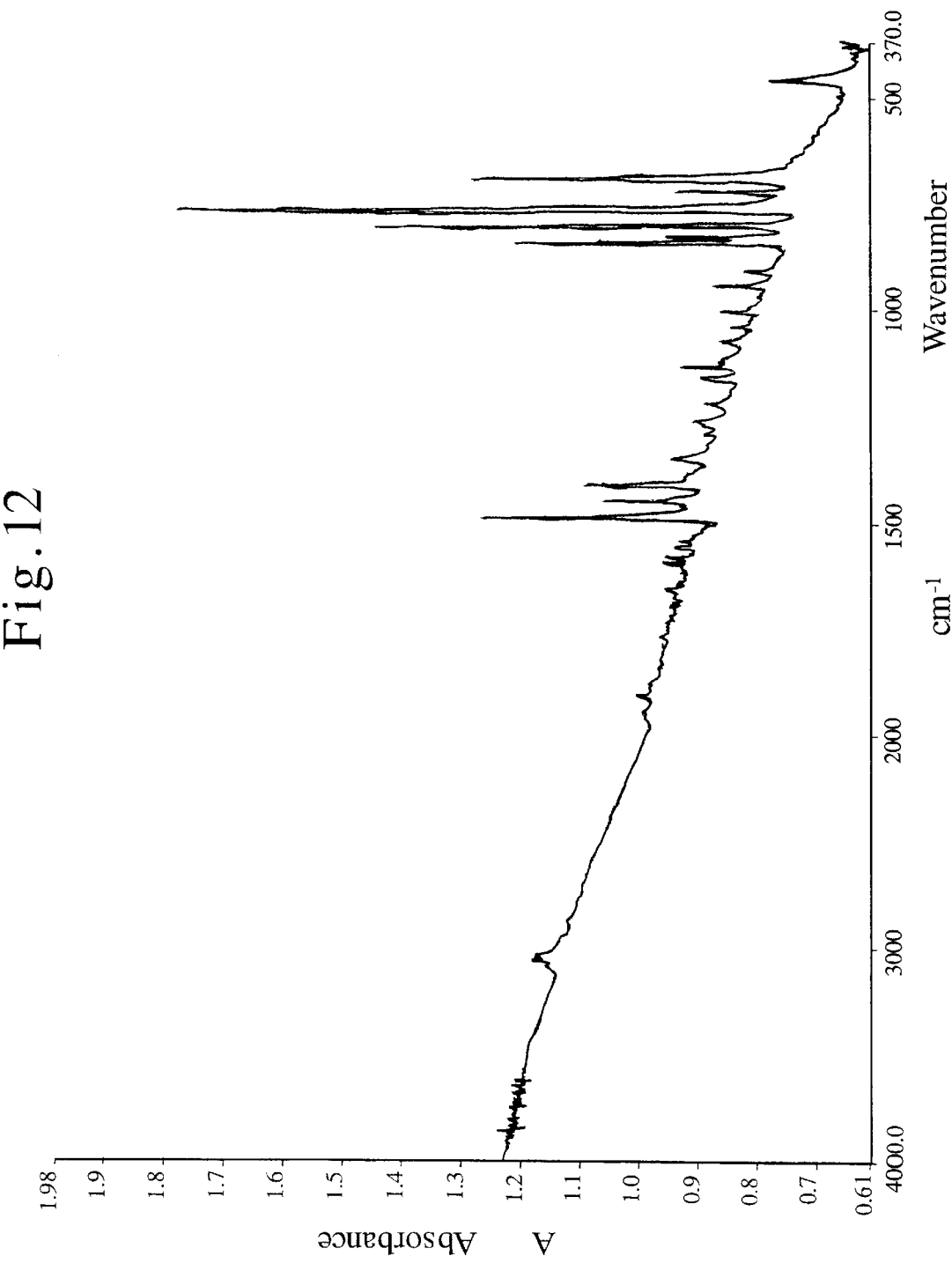
FIG. 12 is a view showing an infrared spectrum of a molecular compound (compound K) according to an eleventh Example of the present invention.

FIG. 12 shows an infrared spectrum of the compound K. In FIG. 12, peaks at 1445.9 $cm^{-1}$ and 800.7 $cm^{-1}$ were assigned to ring stretching vibration and CH out-of-plane bending vibration of the 2,5-di-substituted thiophene ring. Peaks at 1484.9 $cm^{-1}$ and 1409.0 $cm^{-1}$ were assigned to ring stretching vibration of the mono-substituted benzene ring and the 1,4-di-substituted benzene ring in the 4-biphenylyl group, respectively. Furthermore, peaks at 759.9 $cm^{-1}$ and 687.1 $cm^{-1}$ were assigned to CH out-of plane bending vibration of the mono-substituted benzene ring in the same 4-biphenylyl group. A peak at 839.4 $cm^{-1}$ was assigned to CH out-of-plane bending vibration of the 1,4-di-substituted benzene ring in the 4-biphenylyl group.

EXAMPLE 12

As a twelfth Example of the present invention, a process for synthesizing another molecular compound having a biphenylyl group at both terminals thereof (referred to compound L hereinafter) will be described. This molecular compound is a new compound having the following molecular structure.

[Compound 45]

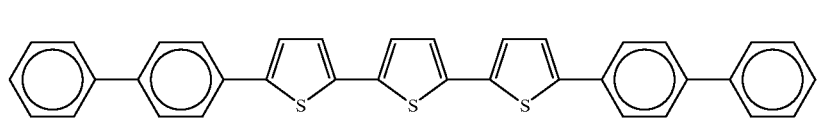

EXAMPLE 11

As an eleventh Example of the present invention, a process for synthesizing a molecular compound having a biphenylyl group at both terminals thereof (referred to compound K hereinafter) will be described. This molecular compound is a new compound having the following molecular structure.

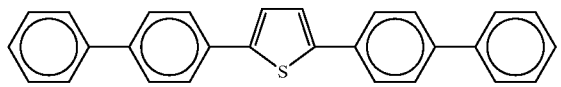

In order to produce this molecular compound, to a 300 mL conical flask were put 335.9 mg (1 mmol) of 2,5-diiodothiophene (made by Aldrich company), 792.1 mg (4 mmol) of 4-biphenylboronic acid (made by Lancaster company) and 138.7 mg (120 μmol) of tetrakis (triphenylphosphine)palladium (0) (made by Aldrich company), together. To this was added 80 mL of benzene and then the solution was heated for dissolution. Furthermore, nitrogen gas was bubbled for 30 minutes to remove dissolved oxygen.

Thereafter, 5 mL of an aqueous solution of 848 mg (8 mmol) of sodium carbonate (made by Wako Pure chemical Industries, Ltd.) was added to the solution, and then the solution was refluxed for 6 hours while the reactor was kept in the state that air was substituted by nitrogen. Subsequently, the reactor was cooled with ice and the In order to produce this molecular compound, to a 50 mL conical flask were put 125.0 mg (0.25 mmol) of 5,5"-diiodo-2,2';5',2"-terthiophene prepared in Example 3, 198.0 mg (1 mmol) of 4-biphenylboronic acid (made by Lancaster company) and 34.7 mg (30 μmol) of tetrakis (triphenylphosphine)palladium (0) (made by Aldrich company), together. To this was added 20 mL of 1,2,4-trichlorobenzene and then the solution was heated for dissolution. Furthermore, nitrogen gas was bubbled for 30 minutes to remove dissolved oxygen.

Thereafter, 5 mL of an aqueous solution of 212 mg (2 mmol) of sodium carbonate (made by Wako Pure chemical Industries, Ltd.) was added to the solution, and then the solution was stirred at 80° C. one day and night while the reactor was kept in the state that air was substituted by nitrogen. Subsequently, the reactor was cooled with ice and the reaction solution was quenched with 0.5 mL aqueous hydrogen peroxide solution. The reaction solution wag filtered and then the resultant golden precipitation was sufficiently washed with acetone to obtain 130 mg of a solid of 5,5"-bis(4-bi-phenylyl)-2,2';5',2"-terthiophene (compound L).

Figure 13:
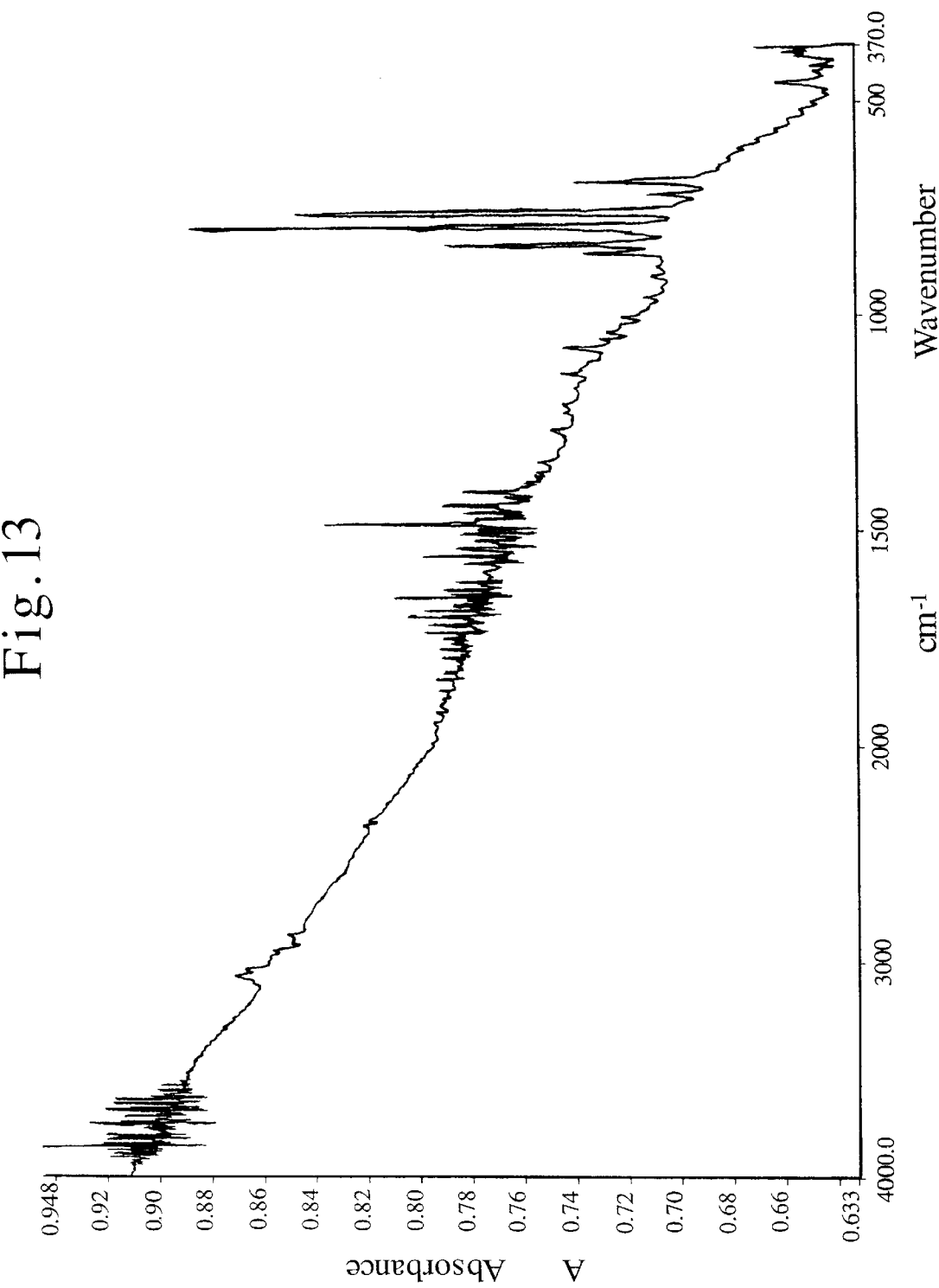
FIG. 13 is a view showing an infrared spectrum of a molecular compound (compound L) according to a twelfth Example of the present invention.

FIG. 13 shows an infrared spectrum of the compound L. In FIG. 13, peaks at 1442.1 $cm^{-1}$ and 792.5 $cm^{-1}$ were assigned to ring stretching vibration and CH out-of-plane bending vibration of the 2,5-di-substituted thiophene ring. Peaks at 1484.4 $cm^{-1}$ and 1408.4 $cm^{-1}$ were assigned to ring stretching vibration of the mono-substituted benzene ring and the 1,4-di-substituted benzene ring in the 4-biphenylyl group, respectively. Furthermore, peaks at 760.8 $cm^{-1}$ and 688.7 cm$^{-1}$ were assigned to CM out-of-plane bending vibration of the mono-substituted benzene ring in the same 4-biphenylyl group. A peak at 835.1 cm$^{-1}$ was assigned to CH out-of-plane bending vibration of the 1,4-di-substituted benzene ring in the 4-biphenylyl group.

EXAMPLE 13

As a thirteenth Example of the present invention, a process for synthesizing still another molecular compound having a biphenyl group at both terminals thereof (referred to compound M hereinafter) will be described. This molecular compound is a new compound having the following molecular structure.

[Compound 46]

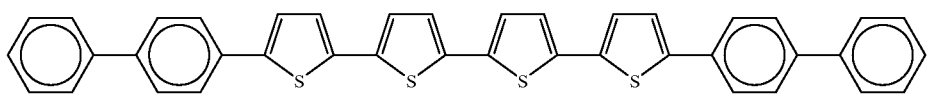

In order to produce this molecular compound, 5-(4-biphenylyl)-2,2'-bithiophene (compound G) obtained in Example 6 was used. That is, 318.5 mg (1 mmol) of 5-(4-biphenylyl)-2,2'-bithiophene, and 296.0 mg (1.25 mmol) of N-iodosuccinimide (made by Aldrich company) were dissolved into 50 mL of methylene chloride, and then 72 μL of acetic acid was added thereto. The solution was stirred over an ice bath for 2 hours. The produced precipitation was filtered and sufficiently washed with methanol to obtain 293 mg (0.66 mmol) of a yellow crystal of 5-(4-biphenylyl)-5'-iodo-2,2'-bithiophene.

Next, to a 30 mL one-neck eggplant type flask were added 172.5 mg (0.264 mmol) of bis(triphenylphosphine)nickel (II) dichloride (made by Tokyo Kasei Co., Ltd.), 974.2 mg (2.64 mmol) of tetrabutylammonium iodide (Tokyo Kasei Co., Ltd.) and 344.9 mg (5.28 mmol) of zinc powder, and the flask was vacuum-sucked and mildly heated with a heat gun to be dried. To this was added 15 mL of distilled tetrahydrofuran, and then the solution was stirred so that the color of the solution changed to red brown.

To this solution was added 293 mg (0.66 mmol) of the 5-(4-biphenylyl)-5'-iodo-2,2'-bithiophene crystal obtained above, in a solid form. The solution was stirred for 27 hours while being heated at 80° C. Thereafter, the reaction solution was cooled to room temperature and then 6 mL of 2 N hydrochloric acid was added thereto. The solution was sufficiently stirred to finish the reaction. This was washed with a great deal of methylene chloride to obtain 120 mg of an orange crystal of 5,5'''-bis(4-biphenylyl)-2,2':5',2'':5'',2'''-quaterthiophene (compound M).

Figure 14:
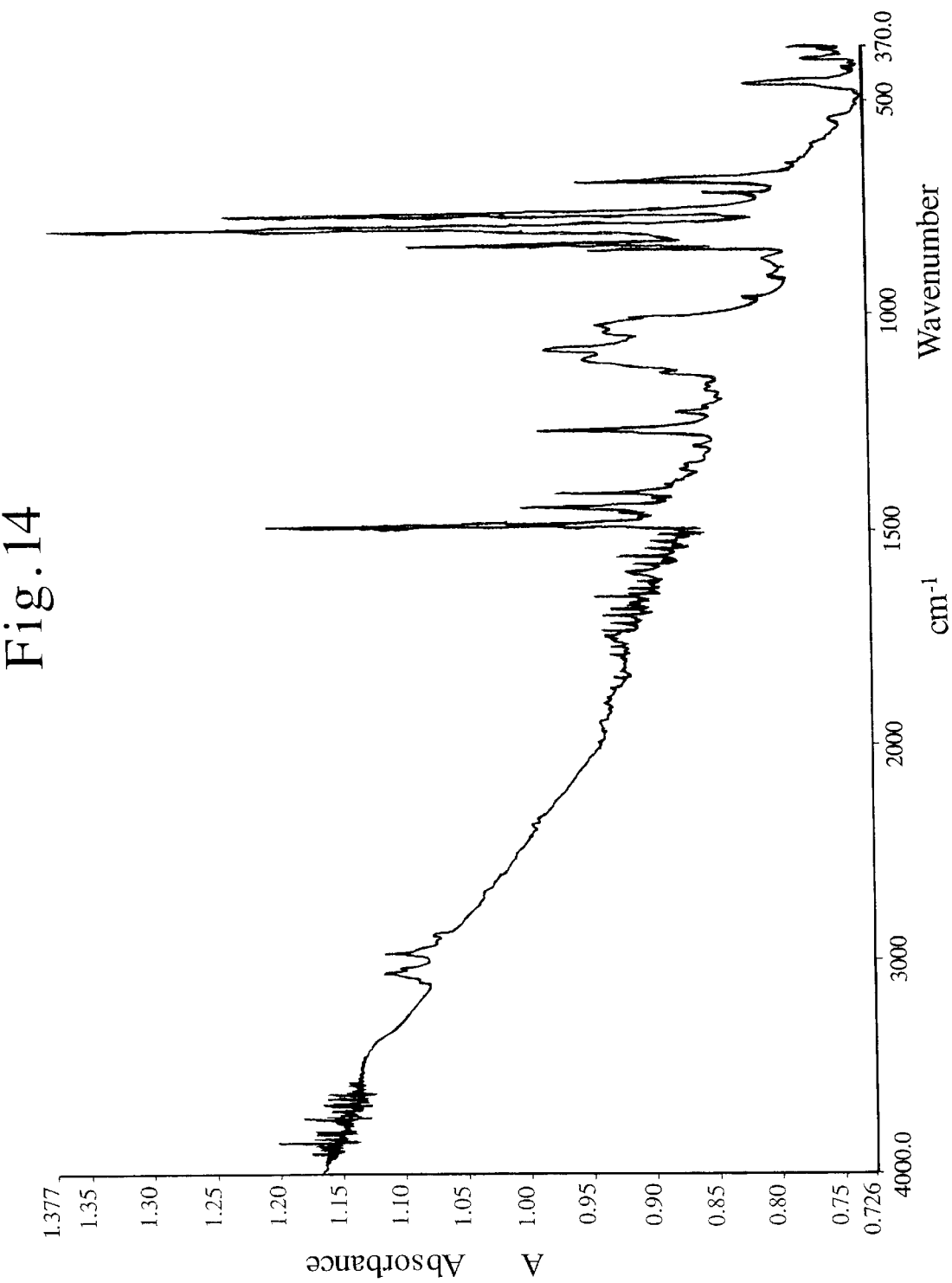
FIG. 14 is a view showing an infrared spectrum of a molecular compound (compound M) according to a thirteenth Example of the present invention.

FIG. 14 shows an infrared spectrum of the compound M. In FIG. 14, peaks at 1441.4 cm$^{-1}$ and 792.2 cm$^{-1}$ were assigned to ring stretching vibration and CH out-of-plane bending vibration of the 2,5-di-substituted thiophene ring, respectively. Peaks at 1484.7 cm$^{-1}$ and 1407.9 cm$^{-1}$ were assigned to ring stretching vibration of the mono-substituted benzene ring and 1,4-di-substituted benzene ring in the 4-biphenylyl group, respectively. Furthermore, peaks at 759.7 cm$^{-1}$ and 688.4 cm$^{-1}$ were assigned to CH out-of-plane bending vibration of the mono-substituted benzene ring in the same 4-biphenylyl group. A peak at 833.8 cm$^{-1}$ was assigned to CH out-of-plane bending vibration of the 1,4-di-substituted benzene ring in the 4-biphenylyl group.

EXAMPLE 14

As a fourteenth Example of the present invention, a process for synthesizing a molecular compound having a tolyl group at both terminals thereof (referred to compound N hereinafter) will be described. This molecular compound is a new compound having the following molecular structure.

[Compound 47]

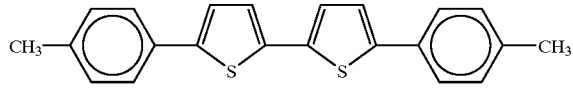

In order to produce this molecular compound, to a 300 mL conical flask were put 418.1 mg (1 mmol) of 5,5'-diiodo-2,2'-bithiophene synthesized in the manner described in Example 2, 543.8 mg (4 mmol) of 4-methylbenzeneboronic acid (made by Lancaster company) and 138.7 mg (120 μmol) of tetrakis(triphenylphosphine)palladium (0) (made by Aldrich company), together. To this was added 80 mL of benzene and the solution was heated for dissolution. Furthermore, nitrogen gas was bubbled for 30 minutes to remove dissolved oxygen.

Thereafter, 5 mL of an aqueous solution of 848 mg (8 mmol) of sodium carbonate (made by Wako Pure chemical Industries, Ltd.) was added to the solution, and then the solution was stirred at room temperature two days and nights while the reactor was kept in the state that air was substituted by nitrogen. Subsequently, the reactor was cooled with ice and the reaction solution was quenched with 1 mL of an aqueous hydrogen peroxide solution. The reaction solution was filtered and then the resultant yellow precipitation was sufficiently washed with methanol to obtain 305 mg of a solid of 5,5'-bis(o-tolyl)-2,2'-bithiophene(compound N).

Figure 15:
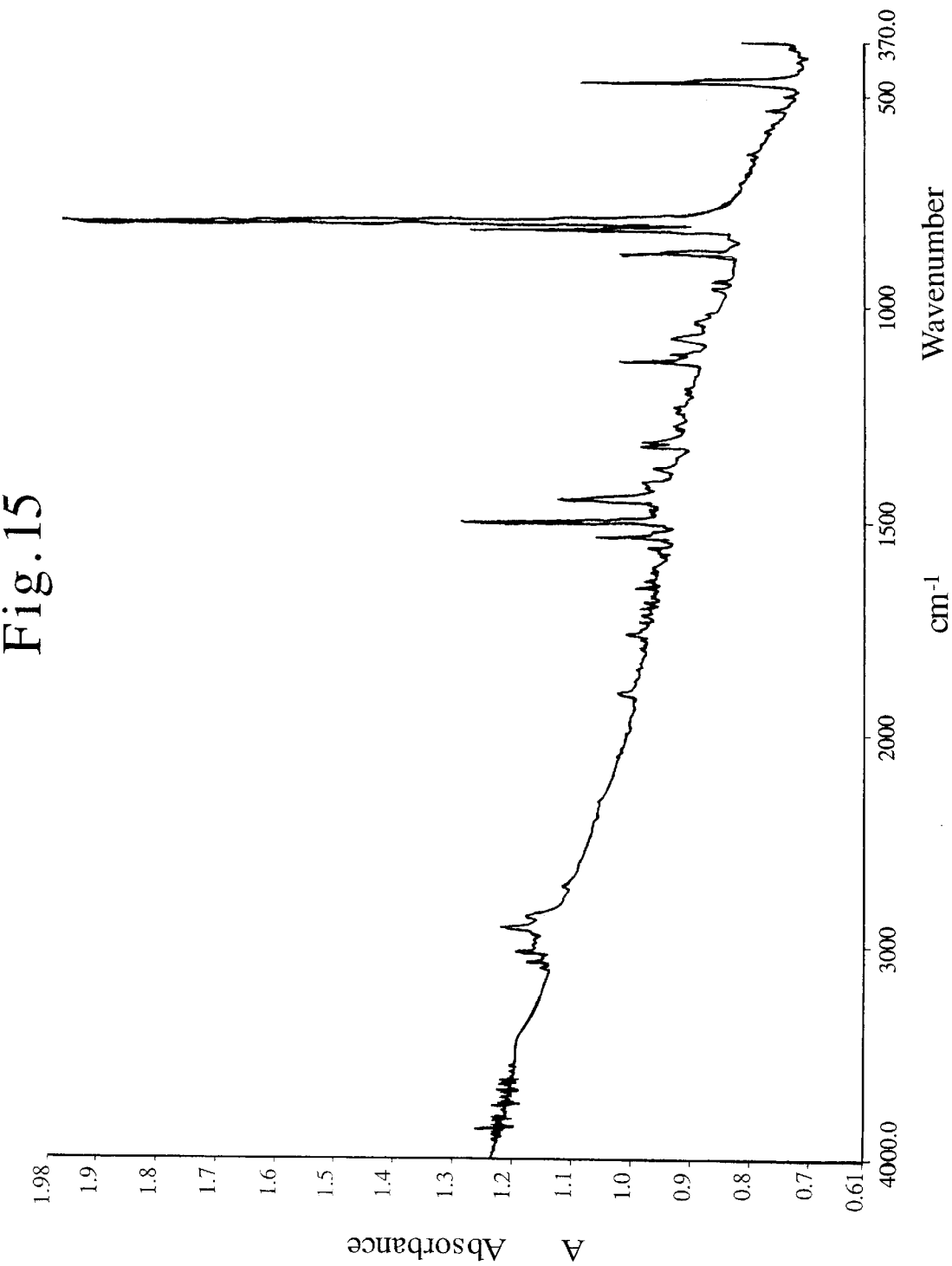
FIG. 15 is a view showing an infrared spectrum of a molecular compound (compound N) according to a fourteenth Example of the present invention.

FIG. 15 shows an infrared spectrum of the compound N. In FIG. 15, peaks at 1447.9 cm$^{-1}$ and 797.5 cm$^{-1}$ were assigned to ring stretching vibration and CH out-of-plane bending vibration of the 2,5-di-substituted thiophene ring, respectively. Peaks at 1499.1 cm$^{-1}$ and 818.4 cm$^{-1}$ were assigned to ring stretching vibration and CH out-of-plane bending vibration of the o-tolyl group, respectively.

EXAMPLE 15

As a fifteenth Example of the present invention, a process for synthesizing a molecular compound having a naphthyl group at both terminals thereof (referred to compound O hereinafter) will be described. This molecular compound is a new compound having the following molecular structure.

[Compound 48]

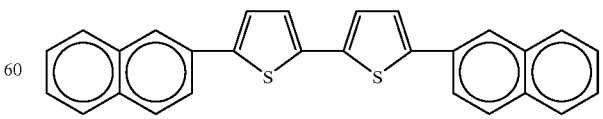

In order to produce this molecular compound, to a 50 mL conical flask were put 209 mg (0.5 mmol) of 5,5'-diiodo-2,2'-bithiophene synthesized in the manner described in Example 2, 344 mg (2 mmol) of 2-naphthaleneboronic acid (made by Lancaster company) and 69.3 mg (60 μmol) of tetrakis(triphenylphosphine)palladium (0) (made by Aldrich company), together. To this was added 20 mL of chlorobenzene and the solution was heated for dissolution. Furthermore, nitrogen gas was bubbled for 30 minutes to remove dissolved oxygen.

Thereafter, 5 mL of an aqueous solution of 424 mg (4 mmol) of sodium carbonate (made by Wako Pure Chemical Industries, Ltd.) was added to the solution, and then the solution was stirred at 80° C. for 6 hours while the reactor was kept in the state that air was substituted by nitrogen. Subsequently, the reactor was cooled with ice and the reaction solution was quenched with 0.5 mL of an aqueous hydrogen peroxide solution. The reaction solution was filtered and then the resultant yellow precipitation was sufficiently washed with acetone to obtain 190 mg of a solid of 5,5'-bis(2-naphthyl)-2,2'-bithiophene (compound O).

Figure 16:
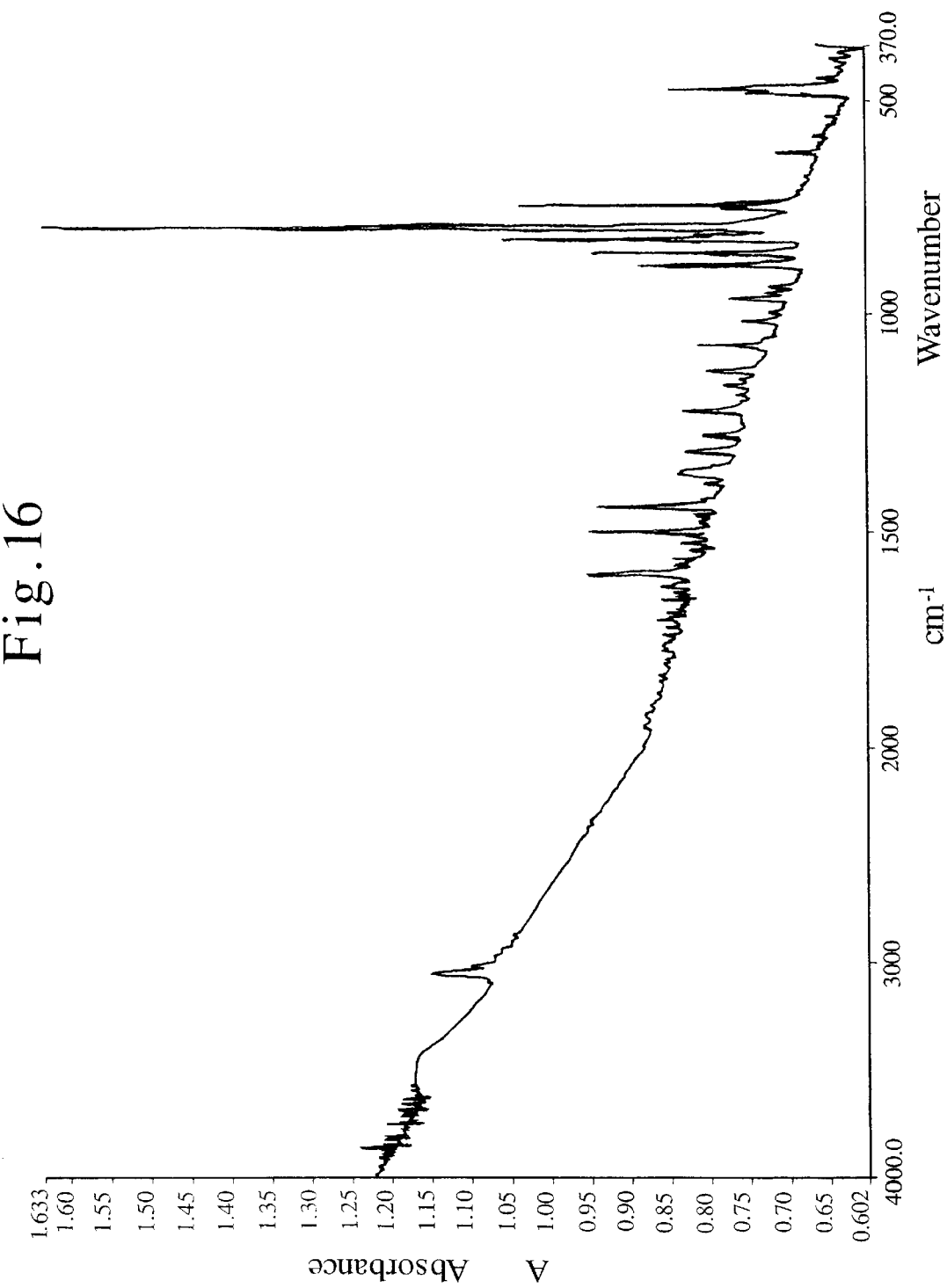
FIG. 16 is a view showing an infrared spectrum of a molecular compound (compound O) according to a fifteenth Example of the present invention.

FIG. 16 shows an infrared spectrum of the compound O. In FIG. 16, peaks at 144.1 $cm^{-1}$ and 794.9 $cm^{-1}$ were assigned to ring stretching vibration and CH out-of-plane bending vibration of the 2,5-di-substituted thiophene ring, respectively. Peaks at 1594.9 $cm^{-1}$ and 1497.6 $cm^{-1}$ were assigned to ring stretching vibration of the 2-naphthyl group. Peaks at 741.8 $cm^{-1}$ and 857.0 $cm^{-1}$ were assigned to CH out-of-plane bending vibration of the same 2-naphthyl group.

EXAMPLE 16

As a sixteenth Example of the present invention, a process for synthesizing another molecular compound having a naphthyl group at both terminals thereof (referred to compound P hereinafter) will be described. This molecular compound is a new compound having the following molecular structure.

[Compound 49]

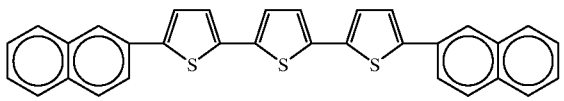

In order to produce this molecular compound, to a 50 mL conical flask were put 125.0 mg (0.25 mmol) of 5,5'-diiodo-2,2':5',2''-tertiophene synthesized in the manner described in Example 3, 172.0 mg (1 mmol) of 2-naphthaleneboronic acid (made by Lancaster company) and 34.7 mg (30 μmol) of tetrakis(triphenylphosphine)palladium (0) (made by Aldrich company), together. To this was added 20 mL of 1,2,4-trichlorobenzene and the solution was heated for dissolution. Furthermore, nitrogen gas was bubbled for 30 minutes to remove dissolved oxygen.

Thereafter, 5 mL of an aqueous solution of 212 mg (2 mmol) of sodium carbonate (made by Wako Pure Chemical Industries, Ltd.) was added to the solution, and then the solution was stirred at 80° C. one day and night while the reactor was kept in the state that air was substituted by nitrogen. Subsequently, the reactor was cooled with ice and the reaction solution was quenched with 0.5 mL of an aqueous hydrogen peroxide solution. The reaction solution was filtered and then the resultant golden precipitation was sufficiently washed with acetone to obtain 80 mg of a solid of 5,5''-bis(2-naphthyl)-2,2':5',2''-terthiophene (compound P).

Figure 17:
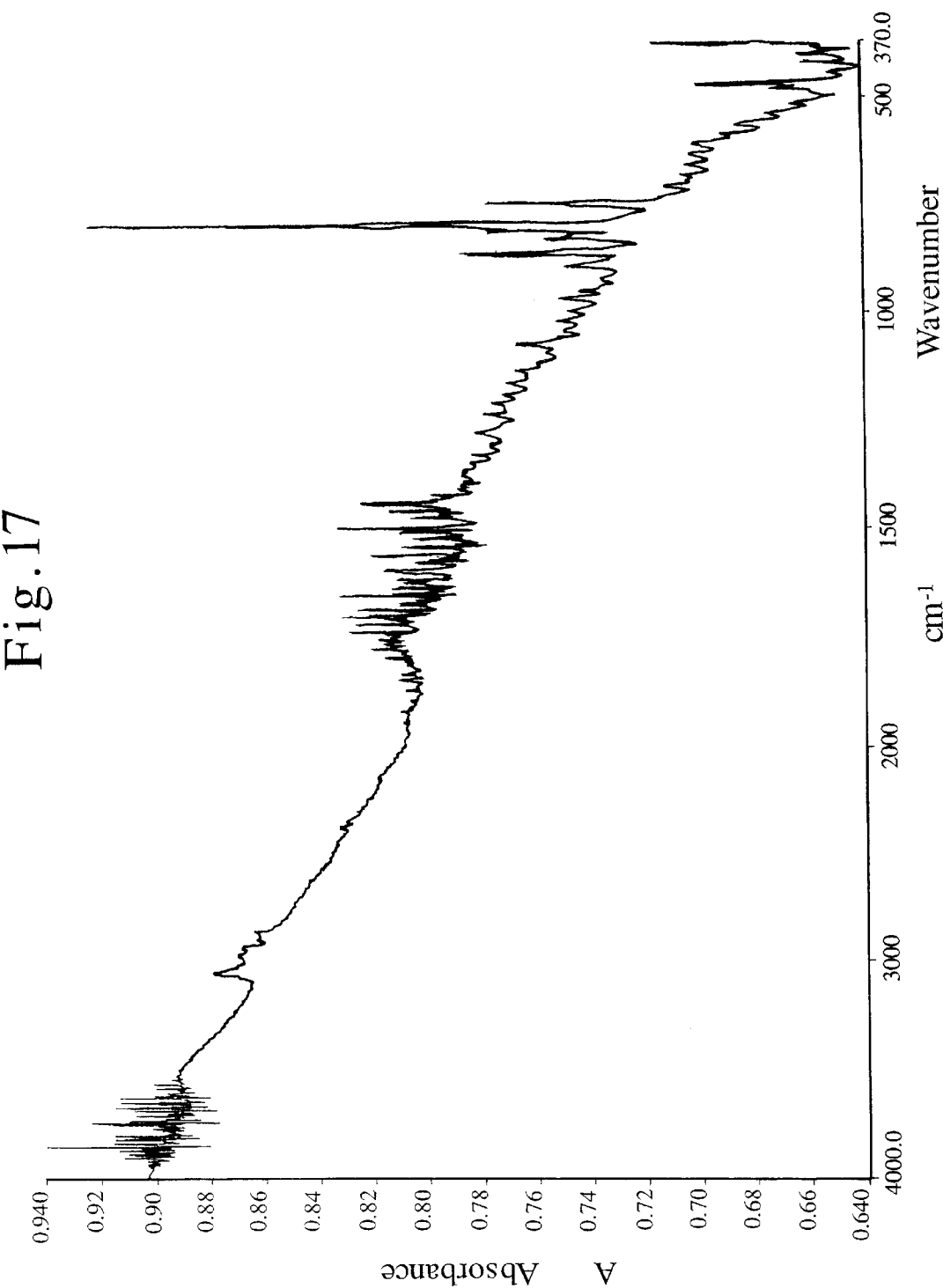
FIG. 17 is a view showing an infrared spectrum of a molecular compound (compound P) according to a sixteenth Example of the present invention.

FIG. 17 shows an infrared spectrum of the compound P. In FIG. 17, peaks at 1438.5 $cm^{-1}$ and 791.8 $cm^{-1}$ were assigned to ring stretching vibration and CH out-of-plane sending vibration of the 2,5-di-substituted thiophene ring, respectively. Peaks at 1595.2 $cm^{-1}$ and 1497.9 $cm^{-1}$ were assigned to ring stretching vibration of the 2-naphthyl group. Peaks at 741.5 $cm^{-1}$ and 859.7 $cm^{-1}$ were assigned to CH out-of-plane bending vibration. of the same 2-naphthyl group.

EXAMPLE 17

The compounds described in the above-mentioned Examples were subjected to elemental analysis and measurement of their melting point. These results are shown in Table 4.

TABLE 4

Elementary analysis and melting points

| Compound | Elementary analysys(%) | Melting point (C°) |
|---|---|---|
| Compound A | C:71.57, H:3.79, S:23.37 (C:71.96, H:4.03, S:24.01) | 279.2 |
| Compound B | C:69.02, H:3.70, S:26.26 (C:69.67, H:3.76, S:26.57) | 335.6 |
| Compound C | C:66.82, H:3.39, S:28.65 (C:68.05, H:3.57, S:28.38) | |
| Compound D | C:80.48, H:4.62, S:13.75 (C:81.66, H:4.71, S:13.63) | 357.9 |
| Compound F | C:78.57, H:4.47, S:16.25 (C:79.15, H:4.60, S:16.25) | 303.7 |
| Compound G | C:75.99, H:4.27, S:19.07 (C:75.43, H:4.43, S:20.14) | 226.1 |
| Compound J | C:68.94, H:3.67, S:26.49 (C:66.63, H:3.73, S:29.64) | |
| Compound K | C:86.00, H:5.11, S:8.27 (C:86.56, H:5.19, S:8.25) | 328.6 |
| Compound L | C:77.50, H:4.38, S:17.68 (C:78.22, H:4.38, S:17.40) | |
| Compound N | C:76.34, H:5.06, S:17.84 (C:76.26, H:5.23, S:18.51) | |

EXAMPLE 18

The present Example will describe the fact that the compounds described in the above-mentioned Examples are useful as luminous materials.

Several solid pieces of samples were taken out with a spatula from the above-mentioned Examples. The samples were put into sample tubes and then the tubes are sealed. these sample tubes were irradiated with ultraviolet rays (wavelength: 365 nm) from an ultraviolet lamp, and then the color tone and brightness of fluorescence emitted from the samples were measured with eyes. The results are shown in Table 5.

TABLE 5

Color tone and brightness of fluorescence

| Compound | Color tone | Brightness |
|---|---|---|
| Compound of Example 10 (Compound I) | Crimson | Very intense |
| (Compound J) | Yellow | Intense |
| Compound of Example 11 (Compound K) | Green | Very intense |
| Compound of Example 12 (Compound L) | Orange | Very intense |
| Compound of Example 13 (Compound M) | Red | Intense |
| Compound of Example 14 (Compound N) | Yellowish green | Very intense |
| Compound of Example 15 (Compound O) | Yellowish orange | Very Intense |
| Compound of Example 16 (Compound P) | Orange | Intense |

The following will describe Examples wherein the molecular compounds of the present invention are used as organic electroluminescence elements.

EXAMPLE 19

A transparent substrate on which an indium thin oxide (ITO) was beforehand formed as a transparent electrode was sufficiently washed. The washed substrate and raw materials were set into a vacuum-evaporation device, and then the device was degassed up to $10^{-4}$ Pa. Thereafter, N,N'-diphenyl-N,N'-bis(3-methylphenyl)-1,1'-biphenyl-4,4'-diamine (referred to as TPD hereinafter) was made up to a film of 50 nm thickness, as a hole transport layer, by a resistance heating evaporation method. Subsequently, the compound B was made up to a thin film of 50 nm thickness, as a luminous layer. Furthermore, a magnesium/silver electrode was vapor-deposited as an electrode to produce an organic electroluminescence element.

When a voltage was applied to the resultant element, uniformly yellow luminescence, the peak of which was at 573 nm, was emitted. The efficiency at 100 $cd/m^2$ was 0.5 lm/W.

EXAMPLE 20

An electroluminescence element was produced in the same manner as in Example 19, except that the compound C was used as the luminous layer. When a voltage was applied to the resultant element, uniformly orange luminescence, the peak of which was at 603 nm, was emitted.

EXAMPLE 21

A transparent substrate on which an indium thin oxide (ITO) was beforehand formed as a transparent electrode was sufficiently washed. The washed substrate and raw materials were set into a vacuum-evaporation device, and then the device was degassed up to $10^{-4}$ Pa. Thereafter, TPD was made up to a layer of 50 nm thickness, as a hole transport layer, by a resistance heating evaporating method. The compound B was then made up to a film of 25 nm thickness, as a luminous layer, and then tris(8-hydroxyquinoline) aluminum (referred to as Alq hereinafter) was made up to a layer of 25 nm, as an electron transport layer, in the same manner. Furthermore, a magnesium/silver electrode was vapor-deposited as an electrode to produce an organic electroluminescence element.

When a voltage was applied to the resultant element, uniformly yellow luminescence, the peak of which was at 570 nm, was emitted.

EXAMPLE 22

An electroluminescence element was produced in the same manner as in Example 21, except that the compound C was used as the luminous layer. When a voltage was applied to the resultant element, uniformly orange luminescence, the peak of which was at 602 nm, was emitted.

EXAMPLE 23

A transparent substrate on which an indium thin oxide (ITO) was beforehand formed as a transparent electrode was sufficiently washed. The washed substrate and raw materials were set into a vacuum-evaporation device, and then the device was degassed up to $10^{-4}$ Pa. Thereafter, TPD was made up to a layer of 50 nm thickness, as a hole transport layer, by resistance heating evaporating method. A mixture film of the compound B and Alq was then made up to a film of 25 nm thickness, as a luminous layer, by co-evaporation. The concentration of the compound B in the Alq was 1 mol %. Subsequently, Alq was vapor-deposited to form an electron transport layer of 25 nm thickness. Furthermore, a magnesium/silver electrode was vapor-deposited as an electrode to produce an organic electroluminescence element.

When a voltage was applied to the resultant element, uniformly green luminescence, the peaks of which were at 508 and 540 nm, was emitted. The efficiency at 100 $cd/m^2$ was 2.5 1 m/W When this device was continuously driven at an initial brightness of 1000 $cd/m^2$, the time during which the brightness became 500 $cd/m^2$, which was a half of the initial brightness, was 100 hours. The time will be referred to as a brightness half-time.

EXAMPLE 24

An organic electroluminescence element was produced in the same manner as in Example 23 except that a mixture film of Alq and the compound C was used as a luminous layer. When a voltage was applied to the resultant element, uniformly yellow luminescence, the peaks of which were at 538 and 568 nm, was emitted. The efficiency at 100 $cd/m^2$ was 4.0 1 m/W. When this device was continuously driven at an initial brightness of 1000 $cd/m^2$, its brightness half-time was 120 hours.

Comparative Example

As a Comparative Example, an organic electroluminescence element was produced as follows. TPD of 50 nm thickness, as a hole transport layer, was deposited on a glass substrate on which ITO was beforehand formed, and then Alq of 50 nm thickness, as a luminous and electron transport layer, was deposited thereon resistance heating evaporating method. Furthermore, a magnesium/silver electrode was vapor-deposited thereon. When a voltage was applied to this element, uniformly green luminescence the peak of which was at 530 nm, was emitted. The efficiency at 100 $cd/m^2$ was 1.5 lm/W. When this device was continuously driven at an initial brightness of 1000 $cd/m^2$, its brightness half-time was 25 hours.

As is understood from Examples 19–24, the organic electroluminescence element of the present invention is used to attain multicolor easily. In particularly, by combining the molecular compound of the present invention with other compounds, it is possible to easily realize an element having an action property of higher efficiency and stability for a long time than conventional elements.

What is claimed is:

1. A luminous material comprising (1) a molecular compound having the following molecular structure:

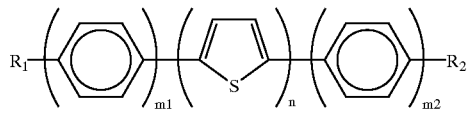

wherein R1 and R2 each independently represents any one of hydrogen, an alkyl group, an alkenyl group and a halogen; and n, m1 and m2 are 1 or more, and (2) at least one additional component, wherein said molecular compound (1) is present in an amount sufficient to provide said luminous material with luminescence.

2. An organic electroluminescence element having at least a luminous layer sandwiched between a pair of electrodes, wherein the luminous layer comprises a molecular compound having the following molecular structure:

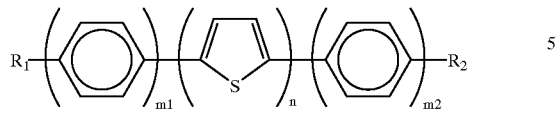

wherein R1 and R2 each independently represents any one of hydrogen, an alkenyl group and a halogen; and m1 and m2 are 1 or more, and n is 4 or more.

3. An organic electroluminescence element having at least a luminous layer sandwiched between a pair of electrodes, wherein the luminous layer comprises a complex of a (1) molecular compound having the following molecular structure:

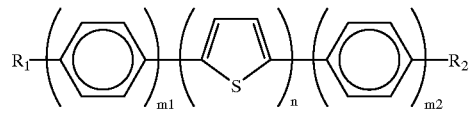

wherein R1 and R2 each independently represents any one of hydrogen, an alkenyl group and a halogen; and m1 and m2 are 1 or more, and n is 4 or more, and
(2) another molecular compound.

* * * * *